(12) United States Patent
Bose et al.

(10) Patent No.: US 12,370,381 B2
(45) Date of Patent: Jul. 29, 2025

(54) SYSTEMS AND METHODS FOR RADIOTHERAPY

(71) Applicant: SHANGHAI UNITED IMAGING HEALTHCARE CO., LTD., Shanghai (CN)

(72) Inventors: Supratik Bose, Houston, TX (US); Jonathan Maltz, Houston, TX (US); Jingjie Zhou, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 254 days.

(21) Appl. No.: 18/171,396

(22) Filed: Feb. 20, 2023

(65) Prior Publication Data
US 2023/0191158 A1 Jun. 22, 2023

Related U.S. Application Data

(63) Continuation of application No. PCT/CN2020/110251, filed on Aug. 20, 2020.

(51) Int. Cl.
*A61N 5/10* (2006.01)
(52) U.S. Cl.
CPC ......... *A61N 5/1039* (2013.01); *A61N 5/1038* (2013.01)
(58) Field of Classification Search
CPC .............................. G16H 20/40; A61N 5/1039
See application file for complete search history.

(56) References Cited

U.S. PATENT DOCUMENTS

| 5,818,902 A | 10/1998 | Yu |
| 10,507,337 B2 | 12/2019 | Willcut et al. |

(Continued)

FOREIGN PATENT DOCUMENTS

| CN | 104548372 A | 4/2015 |
| CN | 107224678 A | 10/2017 |

(Continued)

OTHER PUBLICATIONS

Lu, Renzhi et al., Learning the Relationship Between Patient Geometry and Beam Intensity in Breast Intensity-Modulated Radiotherapy, IEEE Transactions On Biomedical Engineering, 53(5): 908-920, 2006.

(Continued)

*Primary Examiner* — David P Porta
*Assistant Examiner* — Fani Polyzos Boosalis
(74) *Attorney, Agent, or Firm* — METIS IP LLC

(57) ABSTRACT

A method may include obtaining input data relating to a target treatment plan for performing radiotherapy on a lesion using a radiation device. The input data may include a first target image of the lesion. The method may also include obtaining a segment shape estimation model. The method may also include estimating, based on the segment shape estimation model and the input data, a plurality of target location combinations of the target treatment plan and a plurality of target segment shapes of a collimator of the radiation device. One of the plurality of target location combinations may indicate a location of the collimator relative to the lesion. Each of the plurality of target segment shapes may correspond to one of the plurality of target location combinations.

20 Claims, 11 Drawing Sheets

(56) References Cited

U.S. PATENT DOCUMENTS

| | | | |
|---|---|---|---|
| 11,682,485 B2* | 6/2023 | Laaksonen | G06N 3/08 |
| | | | 382/156 |
| 11,896,847 B2* | 2/2024 | Hibbard | A61N 5/1067 |
| 2012/0014507 A1 | 1/2012 | Wu et al. | |
| 2015/0367145 A1 | 12/2015 | Sjolund et al. | |
| 2019/0074079 A1 | 3/2019 | Zankowski et al. | |
| 2019/0192880 A1 | 6/2019 | Hibbard | |
| 2020/0188692 A1 | 6/2020 | Liu | |

FOREIGN PATENT DOCUMENTS

| | | |
|---|---|---|
| CN | 107731298 A | 2/2018 |
| CN | 108771795 A | 11/2018 |

OTHER PUBLICATIONS

Huan-Hsin Tseng et al., The Role of Machine Learning in Knowledge-Based Response-Adapted Radiotherapy, Frontiers in Oncology, 2018, 22 pages.

Vaitheeswaran Ganganathna et al., Determination of Optimal Number of Beams in Direct Machine Parameter Optimization-based Intensity Modulated Radiotherapy for Head and Neck Cases, Journal of Medical Physics, 41(2): 129-134, 2016.

Guy Amit et al., Automatic Learning-Based Selection of Beam Angles in Radiation Therapy of Lung Cancer, IEEE, 230-233, 2014.

Lindsey M. Appenzoller et al., Predicting Dose-volume Histograms for Organs-at-risk in IMRT Planning, Med. Phys., 39(12): 7446-7461, 2012.

M. Mardani et al., Deep-Learning Based Prediction of Achievable Dose for Personalizing Inverse Treatment Planning, International Journal of Radiation Oncology Biology Physics, 96(25): e419-420, 2016.

Chris Mcintosh et al., Voxel-based Dose Prediction with Multi-patient Atlas Selection for Automated Radiotherapy Treatment Planning, Physics in Medicine & Biology, 62: 415-431, 2017.

Rafid Mahmood et al., Automated Treatment Planning in Radiation Therapy using Generative Adversarial Networks, Proceedings of Machine Learning Research, 2018, 14 pages.

Vasant Kearney et al., DoseNet: a Volumetric Dose Prediction Algorithm using 3D Fully-convolutional Neural Networks, Phys. Med. Biol., 2018, 11 pages.

Chen. Xinyuan et al., A Feasibility Study on an Automated Method to Generate Patient-specific Dose Distributions for Radiotherapy using Deep Learning, Med. Phys., 46(1): 56-64, 2019.

A. M. Barragan-Montero et al., Three-Dimensional Dose Prediction for Lung IMRT Patients with Deep Neural Networks: Robust Learning from Heterogeneous Beam Configurations, Medical Physics, 2019, 13 pages.

Dan Nguyen et al., A Feasibility Study for Predicting Optimal Radiation Therapy Dose Distributions of Prostate Cancer Patients from Patient Anatomy using Deep Learning, Scientific Reports, 2019, 10 pages.

Fan, Jiawei et al., Automatic Treatment Planning Based on Three-dimensional Dose Distribution Predicted from Deep Learning Technique, Medical Physics, 2019, 28 pages.

Olaf Ronneberger et al., U-Net: Convolutional Networks for Biomedical Image Segmentation, MICCAI, 234-241, 2015.

Fausto Milletari et al., V-Net: Fully Convolutional Neural Networks for Volumetric Medical Image Segmentation, 2016 Fourth International Conference on 3D Vision, 565-571, 2016.

He, Kaiming et al., Deep Residual Learning for Image Recognition, IEEE, 770-778, 2016.

Mao, Xiao-Jiao et al., Image Restoration Using Very Deep Convolutional Encoder-Decoder Networks with Symmetric Skip Connections, NIPS, 2016, 9 pages.

Vincent S. Khoo et al., Class Solutions for Conformal External Beam Prostate Radiotherapy, Int. J. Radiation Oncology Biol. Phys., 55(4): 1109-1120, 2003.

K. N. Ramamurthy et al., Beyond L2-Loss Functions for Learning Sparse Models, IEEE ICASSP, 2016, 7 pages.

Ma, Yuting et al., Stabilized Sparse Online Learning for Sparse Data, Journal of Machine Learning Research, 18: 1-36, 2017.

James L. Bedford et al., Constrained Segment Shapes in Direct-aperture Optimization for Step-and-shoot IMRT, Med.Phys., 33(4): 944-958, 2006.

Karl Otto, Volumetric Modulated Arc Therapy: IMRT in a Single Gantry Arc, Med.Phys., 35(1): 310-317, 2008.

Yu, Cedric X., Intensity-modulated Arc Therapy with Dynamic Multileaf Collimation: an Alternative to Tomotherapy, Phys. Med. Biol., 40: 1435-1449, 1995.

International Search Report in PCT/CN2020/110251 mailed on Apr. 27, 2021, 5 pages.

Written Opinion in PCT/CN2020/110251 mailed on Apr. 27, 2021, 5 pages.

* cited by examiner

SYSTEMS AND METHODS FOR RADIOTHERAPY

CROSS-REFERENCE TO RELATED APPLICATIONS

This application is a Continuation of International Application No. PCT/CN2020/110251, filed on Aug. 20, 2020, the contents of which are hereby incorporated by reference.

TECHNICAL FIELD

The present disclosure generally relates to radiotherapy, and more particularly, systems and methods for treatment planning.

BACKGROUND

Radiotherapy is used to treat, e.g., cancers and other ailments in biological (e.g., human and animal) tissue using a radiation device. Treatment planning is a process involving determination and/or updating of specific radiotherapy parameters for implementing a treatment goal. The outcome of the treatment planning is a treatment plan. Segment shapes of a collimator of the radiation device is a significant factor in determining an overall delivery time of the treatment plan. Therefore, it is desirable to provide systems and/or methods to efficiently and accurately determine segment shapes for a treatment plan.

SUMMARY

According to a first aspect of the present disclosure, a system may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain input data relating to a target treatment plan for performing radiotherapy on a lesion using a radiation device. The input data may include a first target image of the lesion. The one or more processors may obtain a segment shape estimation model. The one or more processors may estimate, based on the segment shape estimation model and the input data, a plurality of target location combinations of the target treatment plan and a plurality of target segment shapes of a collimator of the radiation device. One of the plurality of target location combinations may indicate a location of the collimator relative to the lesion. Each of the plurality of target segment shapes may correspond to one of the plurality of target location combinations.

In some embodiments, the target treatment plan may include a plurality of control points. Each of the plurality of target location combinations or the plurality of target segment shapes may correspond to one of the plurality of control points.

In some embodiments, the input data may include at least one of a second target image of normal tissue surrounding the lesion, a third target image of the lesion, or target radiation information of the target treatment plan, the target radiation information including at least one of an output dose, a dose output rate, a dose per pulse, or a dose distribution in the lesion.

In some embodiments, the target radiation information may be predicted based on the first target image of the lesion, the second target image of normal tissue surrounding the lesion, and the third target image of the lesion.

In some embodiments, one of the plurality of target location combinations may include a combination of one or more locations where one or more components of the radiation device operate.

In some embodiments, the one of the plurality of target location combination may include a gantry angle of a gantry of the radiation device.

In some embodiments, the one of the plurality of target location combination may include a combination of a gantry angle of a gantry of the radiation device and a collimator angle of the collimator of the radiation device.

In some embodiments, the one of the plurality of target location combination may include a combination of a gantry angle of a gantry of the radiation device, a collimator angle of the collimator of the radiation device, and a position of a couch of the radiation device.

In some embodiments, the collimator may include a plurality of pairs of leaves. One of the plurality of target segment shapes of the collimator may include leaf location of each of the plurality of pairs of leaves.

In some embodiments, the leaf location of one of the plurality of pairs of leaves may include a location of a center of an opening of the pair of leaves and a width of the opening of the pairs of leaves.

In some embodiments, the plurality of target location combinations may be within a plurality of discrete candidate location combinations of a location universal set.

In some embodiments, the segment shape estimation model may be obtained by performing a training process including: obtaining the location universal set including the plurality of candidate location combinations; and determining the segment shape estimation model by iteratively training a preliminary model based on the location universal set.

In some embodiments, obtaining the location universal set including the plurality of candidate location combinations may include: obtaining a plurality of candidate gantry angles, a plurality of candidate collimator angles, or a plurality of candidate couch locations; and obtaining the location universal set based on the plurality of candidate gantry angles, the plurality of candidate collimator angles, or the plurality of candidate couch locations.

In some embodiments, the plurality of target segment shapes may be within a distance universal set including a plurality of discrete candidate leaf locations.

In some embodiments, the training process may include: obtaining the distance universal set including the plurality of candidate leaf locations; and determining the segment shape estimation model by iteratively training the preliminary model based on the distance universal set so that the candidate segment shape corresponding to each of the plurality of candidate location combinations output by the segment shape estimation model is within the distance universal set.

In some embodiments, the plurality of candidate leaf locations may include a plurality of candidate opening locations and a plurality of candidate opening widths.

In some embodiments, the training process includes: obtaining training data including a plurality of training sets.

In some embodiments, obtaining the training data includes: for one of the plurality of training sets, obtaining a historical treatment plan previously generated based on a sample lesion; obtaining a first sample image of the sample lesion corresponding to the historical treatment plan; obtaining sample location combinations and corresponding sample segment shapes in the historical treatment plan; and obtaining the training set based on the first sample image, the sample location combinations, and the sample segment shapes of historical treatment plan.

In some embodiments, obtaining the training set based on the first sample image, the sample location combinations, and the sample segment shapes of the historical treatment plan may include: obtaining processed sample location combinations that are within the location universal set, the processed sample location combinations being obtained by processing the sample location combinations based on the location universal set; obtaining processed sample segment shapes that are within the distance universal set, the processed sample segment shapes being obtained by processing the sample segment shapes based on the distance universal set; obtaining a sample set including the processed sample segment shapes and closed segment shapes, the closed segment shapes corresponding to the candidate location combinations excluding the processed sample location combinations; and obtaining the training set by including the first sample image, the processed sample location combinations, and the sample set of the historical treatment plan.

In some embodiments, the training process may include: initializing the preliminary model; and obtaining the segment shape estimation model by updating the initialized preliminary model using an iteration process including a plurality of iterations, at least one of the plurality of iterations of the iteration process including: obtaining one of the plurality of training sets; generating estimated segment shapes corresponding to the plurality of candidate location combinations by inputting the first sample image of the training set into an intermediate model, the intermediate model being the initialized preliminary model in a first iteration of the plurality of iterations of the iteration process or a previously updated model generated in a previous iteration in the iteration process; determining a value of a loss function based on the estimated segment shapes and the sample set in the training set; determining whether a termination condition is satisfied; in response to determining that the termination condition is not satisfied, generating an updated model by updating the intermediate model based on the value of the loss function; and initiating a next iteration; and designating the intermediate model in a last iteration of the plurality of iterations of the iteration process as the segment shape estimation model.

In some embodiments, the at least one of the plurality of iterations of the iteration process may include: in response to determining that the termination condition is satisfied, terminating the iteration process.

In some embodiments, the value of the loss function may be determined based on sparsity of the sample set, the sparsity of the sample set relating to the closed segment shapes in the sample set.

In some embodiments, the termination condition may relate to at least one of the value of the loss function or a count of iterations of the iteration process that have been performed.

In some embodiments, the training set may include at least one of a second sample image of normal tissue surrounding the sample lesion, a third sample image of the sample lesion, or sample radiation information of the historical treatment plan, the sample radiation information including at least one of a sample output dose, a sample dose output rate, a sample dose per pulse, or a sample dose distribution in the sample lesion.

In some embodiments, the sample radiation information may be predicted based on the first sample image of the sample lesion, the second sample image of normal tissue surrounding the sample lesion, and the third sample image of the sample lesion.

In some embodiments, the at least one of the plurality of iterations of the iteration process may include: generating the estimated segment shapes by inputting at least one of the second sample image, the third sample image, or the sample radiation information of the training set into the intermediate model.

In some embodiments, the at least one of the plurality of iterations of the iteration process may include: determining estimated radiation information based on the estimated segment shapes; comparing the estimated radiation information and the sample radiation information; and generating the updated model by updating the intermediate model based on the comparison.

According to another aspect of the present disclosure, a method may include one or more of the following operations. One or more processors may obtain input data relating to a target treatment plan for performing radiotherapy on a lesion using a radiation device. The input data may include a first target image of the lesion. The one or more processors may obtain a segment shape estimation model. The one or more processors may estimate, based on the segment shape estimation model and the input data, a plurality of target location combinations of the target treatment plan and a plurality of target segment shapes of a collimator of the radiation device. One of the plurality of target location combinations may indicate a location of the collimator relative to the lesion. Each of the plurality of target segment shapes may correspond to one of the plurality of target location combinations.

According to yet another aspect of the present disclosure, a system may include an input obtaining module configured to obtain input data relating to a target treatment plan for performing radiotherapy on a lesion using a radiation device. The input data may include a first target image of the lesion. The system may also include a model obtaining module configured to obtain a segment shape estimation model. The system may also include a shape estimation module configured to estimate, based on the segment shape estimation model and the input data, a plurality of target location combinations of the target treatment plan and a plurality of target segment shapes of a collimator of the radiation device. One of the plurality of target location combinations may indicate a location of the collimator relative to the lesion. Each of the plurality of target segment shapes may correspond to one of the plurality of target location combinations.

According to yet another aspect of the present disclosure, a non-transitory computer readable medium may comprise at least one set of instructions. The at least one set of instructions may be executed by one or more processors of a computing device. The one or more processors may obtain input data relating to a target treatment plan for performing radiotherapy on a lesion using a radiation device. The input data may include a first target image of the lesion. The one or more processors may obtain a segment shape estimation model. The one or more processors may estimate, based on the segment shape estimation model and the input data, a plurality of target location combinations of the target treatment plan and a plurality of target segment shapes of a collimator of the radiation device. One of the plurality of target location combinations may indicate a location of the collimator relative to the lesion. Each of the plurality of target segment shapes may correspond to one of the plurality of target location combinations.

According to yet another aspect of the present disclosure, a system may include one or more storage devices and one or more processors configured to communicate with the one or more storage devices. The one or more storage devices may include a set of instructions. When the one or more processors executing the set of instructions, the one or more processors may be directed to perform one or more of the following operations. The one or more processors may obtain a preliminary model. The one or more processors may obtain training data. The one or more processors may obtain a segment shape estimation model by training the preliminary model based on the training data. The segment shape estimation model may be configured to estimate, based on input data, a plurality of target location combinations in a target treatment plan for performing radiotherapy on a lesion using a radiation device and a plurality of target segment shapes of a collimator of the radiation device. The input data may include a first target image of the lesion. Each of the plurality of target segment shapes may correspond to one of the plurality of target location combinations. One of the plurality of target location combinations may indicate a location of the collimator relative to the lesion.

According to yet another aspect of the present disclosure, a method may include one or more of the following operations. One or more processors may obtain a preliminary model. The one or more processors may obtain training data. The one or more processors may obtain a segment shape estimation model by training the preliminary model based on the training data. The segment shape estimation model may be configured to estimate, based on input data, a plurality of target location combinations in a target treatment plan for performing radiotherapy on a lesion using a radiation device and a plurality of target segment shapes of a collimator of the radiation device. The input data may include a first target image of the lesion. Each of the plurality of target segment shapes may correspond to one of the plurality of target location combinations. One of the plurality of target location combinations may indicate a location of the collimator relative to the lesion.

According to yet another aspect of the present disclosure, a system may include a model obtaining module configured to obtain a preliminary model. The model obtaining module may be also configured to obtain training data. The model obtaining module may be also configured to obtain a segment shape estimation model by training the preliminary model based on the training data. The segment shape estimation model may be configured to estimate, based on input data, a plurality of target location combinations in a target treatment plan for performing radiotherapy on a lesion using a radiation device and a plurality of target segment shapes of a collimator of the radiation device. The input data may include a first target image of the lesion. Each of the plurality of target segment shapes may correspond to one of the plurality of target location combinations. One of the plurality of target location combinations may indicate a location of the collimator relative to the lesion.

According to yet another aspect of the present disclosure, a non-transitory computer readable medium may comprise at least one set of instructions. The at least one set of instructions may be executed by one or more processors of a computing device. The one or more processors may obtain a preliminary model. The one or more processors may obtain training data. The one or more processors may obtain a segment shape estimation model by training the preliminary model based on the training data. The segment shape estimation model may be configured to estimate, based on input data, a plurality of target location combinations in a target treatment plan for performing radiotherapy on a lesion using a radiation device and a plurality of target segment shapes of a collimator of the radiation device. The input data may include a first target image of the lesion. Each of the plurality of target segment shapes may correspond to one of the plurality of target location combinations. One of the plurality of target location combinations may indicate a location of the collimator relative to the lesion.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 2:
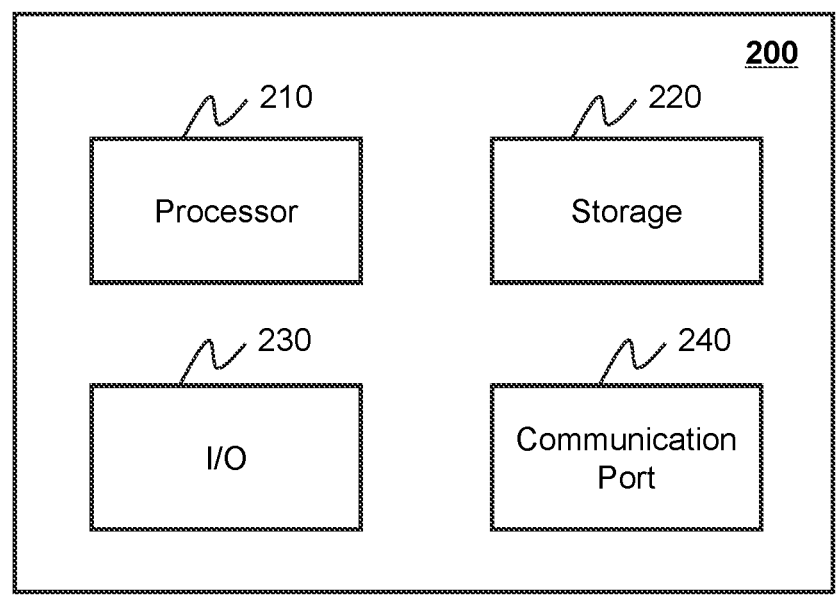
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding a process for exposure controlling. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

In this present disclosure, the terms "radiation therapy," "radiotherapy," "radiation treatment," and "treatment" may be used interchangeably to refer to a therapy for treating, e.g., cancers and other ailments in biological (e.g., human and animal) tissue using radiation. The terms "treatment plan," "therapy plan," and "radiotherapy plan" may be used interchangeably to refer to a plan used to perform radiotherapy.

Figure 1:
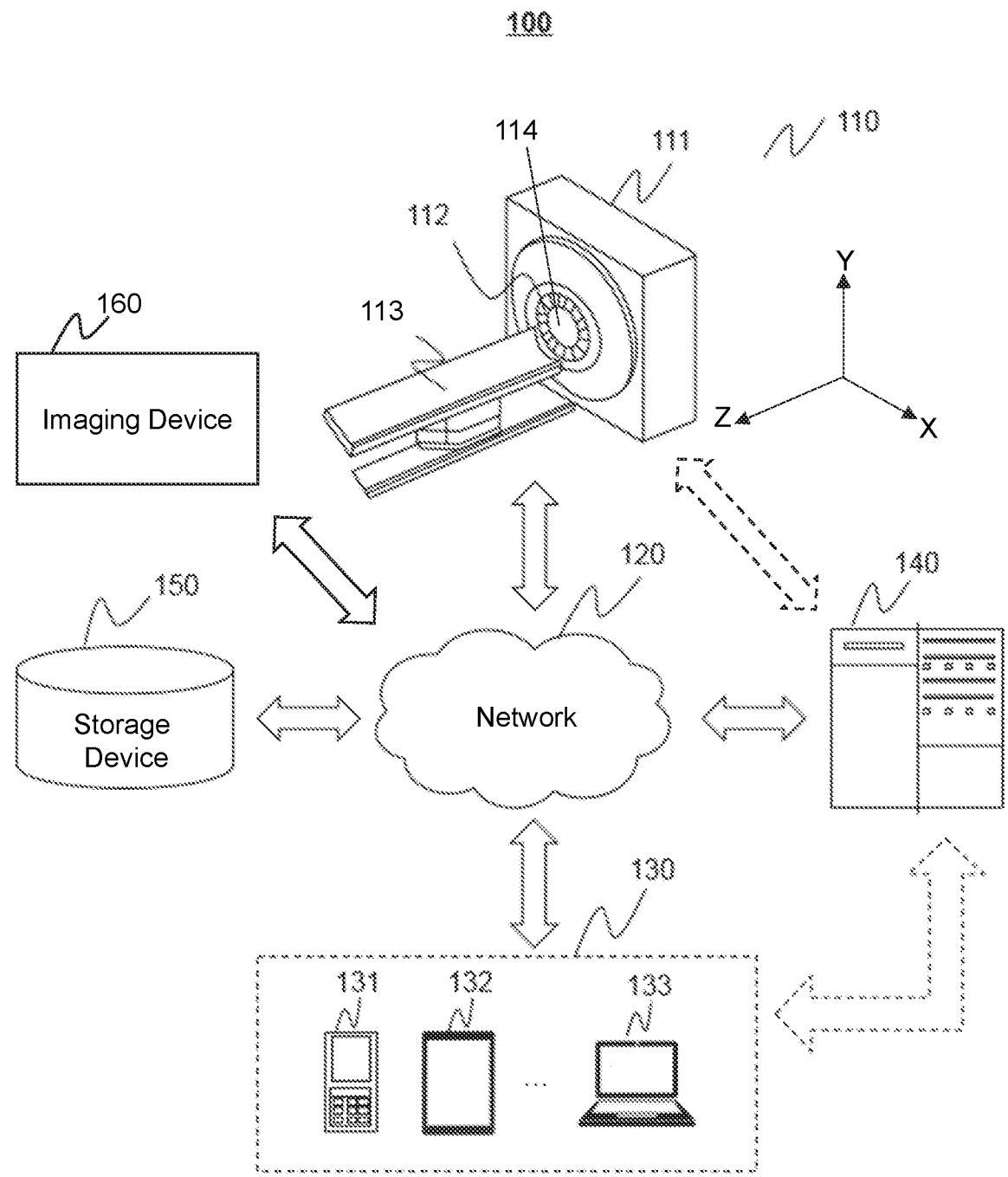
FIG. 1 is a schematic diagram illustrating an exemplary medical radiation system according to some embodiments of the present disclosure.

FIG. 1 is a schematic diagram illustrating an exemplary medical radiation system according to some embodiments of the present disclosure. In some embodiments, the medical radiation system 100 may be applied to any radiotherapy scenario in which a multileaf collimator (MLC) is used. As used herein, the terms "treatment," "radiation treatment," "radiation therapy," and "radiotherapy" are used interchangeably. In some embodiments, the medical radiation system 100 may be applied in intensity modulated radiation therapy (IMRT), intensity modulated arc therapy (IMAT), volume modulated arc therapy (VMAT), image-guided radiotherapy (IGRT), single arc radiotherapy, multi-arc radiotherapy, or the like.

As illustrated in FIG. 1, the medical radiation system 100 may include a radiation device 110, a network 120, one or more terminals 130, a processing device 140, and a storage device 150. In some embodiments, the medical radiation system 100 may further include an imaging device 160. In some embodiments, the radiation device 110 and the imaging device 160 may be integrated into a single device, or separate devices. In some embodiments, the imaging device 160 may be omitted in the medical radiation system 100.

In some embodiments, the components in the medical radiation system 100 may be connected in one or more of various ways. Merely by way of example, the radiation device 110 may be connected to the processing device 140 through the network 120. As another example, the radiation device 110 may be connected to the processing device 140 directly as indicated by the bi-directional arrow in dotted lines linking the radiation device 110 and the processing device 140. As a further example, the storage device 150 may be connected to the processing device 140 directly or through the network 120. As still a further example, the terminal 130 may be connected to the processing device 140 directly (as indicated by the bi-directional arrow in dotted lines linking the terminal 130 and the processing device 140) or through the network 120. As still a further example, the imaging device 160 may be connected to the radiation device 110 directly or through the network 120.

In the present disclosure, the X axis, the Y axis, and the Z axis shown in FIG. 1 may form an orthogonal coordinate system. The X axis and the Z axis shown in FIG. 1 may be horizontal, and the Y axis may be vertical. As illustrated, the positive X direction along the X axis may be from the left side to the right side of the radiation device 110 seen from the direction facing the front of the radiation device 110; the positive Y direction along the Y axis shown in FIG. 1 may be from the lower part to the upper part of the radiation device 110; the positive Z direction along the Z axis shown in FIG. 1 may refer to a direction in which the object is moved out of the couch 113 of the radiation device 110.

In some embodiments, the radiation device 110 may be configured to deliver radiation to a planned target volume (PTV) (also referred to as a target, e.g., a lesion) of an object (e.g., a patient) to treat the object. The radiation device 110 may include a gantry 111, a radiation source 112, and a couch 113. In some embodiments, the radiation source 112 may be connected to the gantry 111 and rotatable around an object (e.g., the Z axis). During radiotherapy performed on an object using the radiation device 110, the object may be placed on the couch 113 and moved into a treatment area of the radiation device 110, such as the treatment area 114 in FIG. 1.

Figure 4:
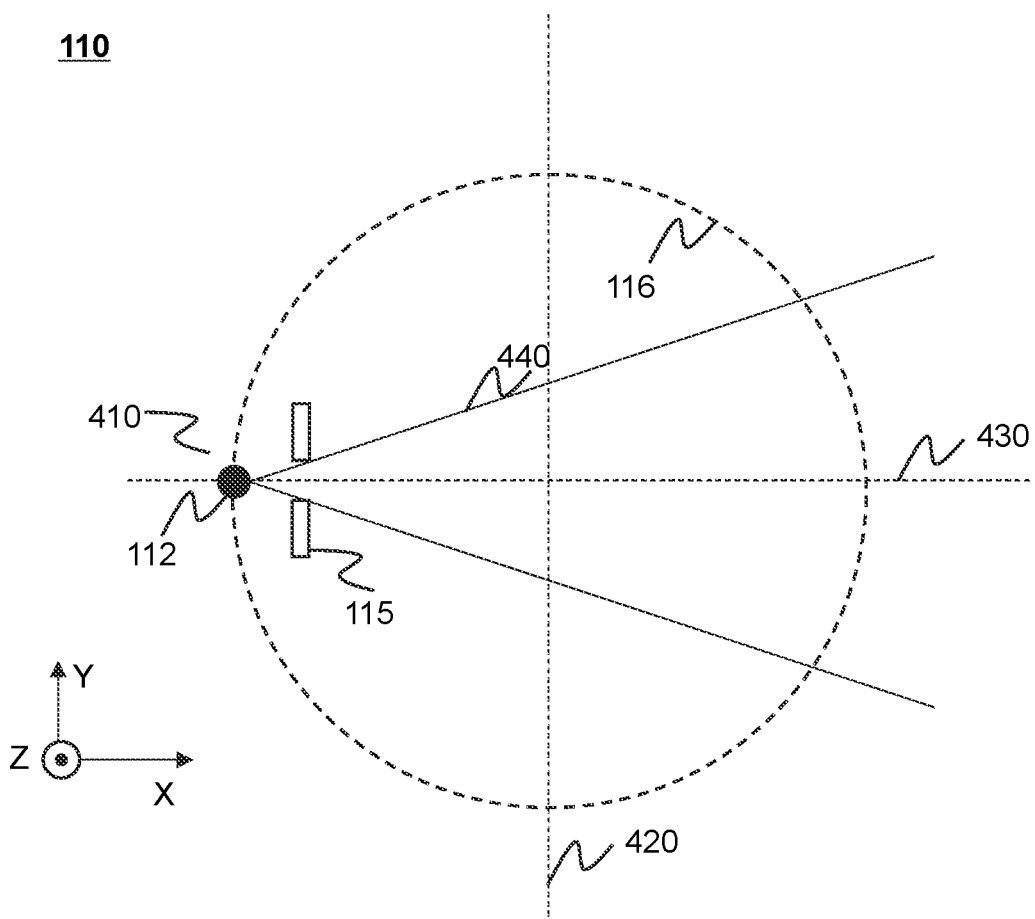
FIG. 4 is a schematic diagram illustrating an exemplary gantry angle according to some embodiments of the present disclosure.

The radiation source 112 may emit radiation rays to an object that is placed in the couch 113. The radiation rays may include X-rays, y-rays, a-rays, ultraviolet, laser, neutron, proton, or the like, or a combination thereof. A multileaf collimator (MLC) 115 (e.g., as shown in FIG. 4) may be attached to the radiation source 112. The MLC 115 may include adjustable leaves that act as a filter, blocking or allowing radiation to pass through, in order to tailor the shape of radiation rays to the shape of a target (e.g., a tumor) of an object while reducing exposure, under the radiation rays, of the neighboring organs at risks (OARs) of the target (e.g., normal tissue immediately surrounding the target). In some embodiments, the MLC 115 may rotate with the radiation source 112. In some embodiments, during rotation, the location of the MLC 115 relative to the radiation source 112 may be constant or substantially constant.

In some embodiments, the object may be biological. Merely by way of example, the object may include a patient, a man-made object, etc. As another example, the object may include a specific portion, organ, and/or tissue of the patient. For example, the object may include head, brain, neck, body, shoulder, arm, thorax, cardiac, stomach, blood vessel, soft tissue, knee, feet, or the like, or any combination thereof. In the present disclosure, "subject" and "object" are used interchangeably.

In some embodiments, the imaging device 160 may be configured to acquire one or more images of a target of an object. In some embodiments, the imaging device 160 may include a single modality imaging device and/or a multi-modality imaging device. The single modality imaging device may include, for example, a magnetic resonance imaging (MRI) device, a computed tomography (CT) device, a positron emission tomography (PET) device, a single photon emission computed tomography (SPECT) device, an ultrasound device, an X-ray device, or the like. The multi-modality imaging device may include, for example, a computed tomography-magnetic resonance imaging (MRI-CT) device, a positron emission tomography-magnetic resonance imaging (PET-MRI) device, a single photon emission computed tomography-magnetic resonance imaging (SPECT-MRI) device, a digital subtraction angiography-magnetic resonance imaging (DSA-MRI) device, a positron emission tomography-computed tomography (PET-CT) device, a single photon emission computed tomography-computed tomography (SPECT-CT) device, etc.

The network 120 may facilitate exchange of information and/or data. In some embodiments, one or more components of the medical radiation system 100 (e.g., the radiation device 110, the terminal 130, the processing device 140, the storage device 150, or the imaging device 160) may send information and/or data to another component(s) in the medical radiation system 100 via the network 120. For example, the processing device 140 may obtain a user instruction from the terminal 130 via the network 120. As another example, the processing device 140 may obtain scan data from the imaging device 160 via the network 120. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof.

Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the medical radiation system 100 may be connected to the network 120 to exchange data and/or information.

The terminal 130 include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smart-phone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the radiation device 110. In some embodiments, the terminal 130 may operate the radiation device 110 via a wireless connection. In some embodiments, the terminal 130 may receive information and/or instructions inputted by a user, and send the received information and/or instructions to the radiation device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the radiation device 110, the terminal 130, the storage device 150, or the imaging device 160. For example, the processing device 140 may determine segment shapes for a treatment plan based on a segment shape estimation model. The processing device 140 may be a central processing unit (CPU), a digital signal processor (DSP), a system on a chip (SoC), a microcontroller unit (MCU), or the like, or any combination thereof.

In some embodiments, the processing device 140 may be a single server or a server group. The server group may be centralized or distributed. In some embodiments, the processing device 140 may be local or remote. For example, the processing device 140 may access information and/or data stored in the radiation device 110, the terminal 130, the imaging device 160, and/or the storage device 150 via the network 120. As another example, the processing device 140 may be directly connected to the radiation device 110, the terminal 130, the imaging device 160, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. For example, the storage device 150 may store one or more images obtained from the imaging device 160. As another example, the storage device 150 may store a segment shape estimation model. In some embodiments, the storage device 150 may store data and/or instructions that the processing device 140 may execute or use to perform exemplary methods described in the present disclosure. For example, the storage device 150 may store instructions that the processing device 140 may execute or use to determine segment shapes for a treatment plan based on a segment shape estimation model. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the medical radiation system 100 (e.g., the radiation device 110, the imaging device 160, the terminal 130, the processing device 140). One or more components of the medical radiation system 100 may access the data or instructions stored in the storage device 150 via the network 120. In some embodiments, the storage device 150 may be directly connected to or communicate with one or more components of the medical radiation system 100 (e.g., the terminal 130, the processing device 140). In some embodiments, the storage device 150 may be part of the processing device 140.

FIG. 2 is a schematic diagram illustrating hardware and/or software components of an exemplary computing device according to some embodiments of the present disclosure. As illustrated in FIG. 2, the computing device 200 may include a processor 210, a storage 220, an input/output (I/O) 230, and a communication port 240. In some embodiments, the processing device 140 and/or the terminal 130 may be implemented on the computing device 200.

The processor 210 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 210 may process data and/or images obtained from the radiation device 110, the terminal 130, the storage device 150, the imaging device 160, and/or any other component of the medical radiation system 100. For example, the processing device 140 may determine segment shapes for a treatment plan based on a segment shape estimation model. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the radiation device 110, the terminal 130, the storage device 150, or any other component of the medical radiation system 100. In some embodiments, the storage 220 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage device 150 may store instructions that the processing device 140 may execute or use to determine segment shapes for a treatment plan based on a segment shape estimation model.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the radiation device 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
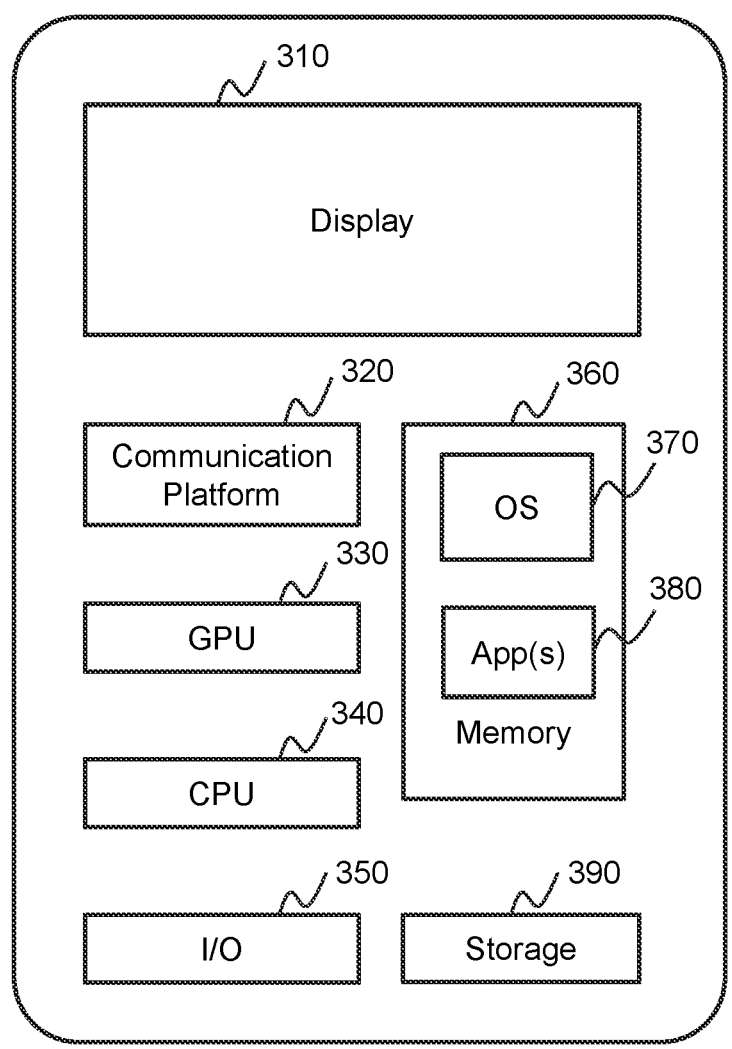
FIG. 3 is a schematic diagram illustrating hardware and/or software components of an exemplary mobile device according to some embodiments of the present disclosure.

FIG. 3 is a schematic diagram illustrating hardware and/or software components of a mobile device according to some embodiments of the present disclosure. In some embodiments, the processing device 140 and/or the terminal 130 may be implemented on the computing device 200. As illustrated in FIG. 3, the mobile device 300 may include a display 310, a communication platform 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the medical radiation system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to control exposure in medical radiation as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Radiotherapy may be used to treat, e.g., cancers and other ailments in biological (e.g., human and animal) tissue. An exemplary radiotherapy may be provided using a radiation device (e.g., the radiation device 110 in FIG. 1), whereby a target (e.g., a tumor) may be irradiated by high-energy particles (e.g., electrons, photons, ions and the like). In a radiation treatment, multiple radiation rays may be directed towards the target from different angles. The target (e.g., a lesion) may be referred to as a planned target volume (PTV). The normal tissue immediately surrounding the target may be referred to as an organ at risk (OAR). Treatment planning may be a process involving determination and/or updating of specific radiotherapy parameters for implementing a treatment goal. The outcome of the treatment planning may be a treatment plan. A treatment planning process may include delineating one or more targets and one or more OARs from one or more medical images of a patient, and specifying the radiotherapy parameters based on the delineating result.

Taking a target treatment plan corresponding to a target treatment performed on a target (e.g., a lesion) of an object (e.g., a patient) by the radiation device 110 in FIG. 1 as an example, radiotherapy parameters of the target treatment plan may include a total time of the target treatment, a total dose during the total time, a plurality of target control points (also referred to as target control time points) within the total time, target radiation information corresponding to each of the plurality of target control points, or the like, or any combination thereof.

In some embodiments, the target radiation information corresponding to each of the plurality of target control points may include a dose output rate, a dose output per pulse, an output dose, a dose distribution in the target, a target location combination, a segment shape, or the like, or any combination thereof.

In some embodiments, the dose distribution in the target corresponding to a target control point may refer to a dose distribution in the target during a time period that ends in the target control point. In some embodiments, the dose output rate corresponding to a target control point may refer to a dose output rate during a time period that ends in the target control point. In some embodiments, the dose output per pulse corresponding to a target control point may refer to a dose output per pulse during a time period that ends in the target control point. In some embodiments, the output dose corresponding to a target control point may refer to the output dose during a time period that ends in the target control point. For example, the time period may be from the start (e.g., the first control point of the plurality of target control points) of the total time to the target control point. As another example, the time period may be between the target control point and a control point prior to the target control point.

In some embodiments, the target location combination or the segment shape corresponding to a target control point may indicate a location of the radiation device 110 at the target control point.

In some embodiments, the target location combination corresponding to a target control point may indicate a location of the MLC 115 relative to the target at the target control point.

In some embodiments, the target location combination corresponding to a target control point may include a combination of one or more locations where one or more components of the radiation device 110 operate at the target control point. For example, the target location combination corresponding to a target control point may include a gantry angle of the radiation source 112 at the target control point. As another example, the target location combination corresponding to a target control point may include a combination (also referred to as a gantry-collimator angle combination) of a gantry angle of the radiation source 112 and a collimator angle of the MLC 115 at the target control point. As still another example, the target location combination corresponding to a target control point may include a combination of a gantry angle of the radiation source 112, a collimator angle of the MLC 115, and a couch location of the couch 113 at the target control point.

In some embodiments, during the target treatment, the radiation source 112 may rotate around the Z axis illustrated in FIG. 1 and deliver radiation rays to the target from different angles. The gantry angle (also referred to as a beam angle) corresponding to a target control point may indicate a location of the radiation source 112 in the radiation device 110 at the target control point. For example, when the radiation source 112 rotates to a location at a target control point, the corresponding gantry angle may refer to an angle between the center line of the radiation rays emitted from the radiation source 112 at the location and a reference direction (e.g., a direction vertical to the ground).

Merely by way of example, FIG. 4 is a schematic diagram illustrating an exemplary gantry angle according to some embodiments of the present disclosure. The radiation device 110 shown in FIG. 4 is a view of the radiation device 110 seen from the direction facing the front of the radiation device 110 (e.g., along the negative Z direction illustrated in FIGS. 1 and 4). The X axis, the Y axis, and the Z axis in FIG. 4 correspond to those in FIG. 1. In FIG. 4, the positive Z direction is represented as a direction that is vertical to the paper and points outward.

As shown in FIG. 4, the radiation source 112 may rotate around the Z axis along the trajectory 116. The MLC 115 may rotate around the Z axis with the radiation source 112. The radiation source 112 may emit radiation rays (or referred to as radiation beams) 440. The center line of the radiation rays 440 is represented by the dashed line 430 in FIG. 4. The dashed line 420 (along the Y direction as illustrated in FIGS. 1 and 4) vertical to the ground may be designated as the reference line. When the radiation source 112 rotates to the location 410, an angle between the reference line 420 and the center line 430 of the radiation rays 440 is 90°. The gantry angle of the radiation source 112 at the location 410 is 90°.

In some embodiments, the MLC 115 of the radiation device 110 may rotate around the Z axis with the radiation source 112 and around the center line (e.g., coinciding with the center line 430 of the radiation rays 440 emitted from the radiation source 112) of the MLC 115. The collimator angle corresponding to a target control point may indicate a location of the MLC 115 relative to the radiation source 112 at the target control point. For example, when the MLC 115 rotates, around its center line, to a location at a target control point, the corresponding collimator angle may refer to an angle between the location and an initial location of the MLC 115.

Figure 5:
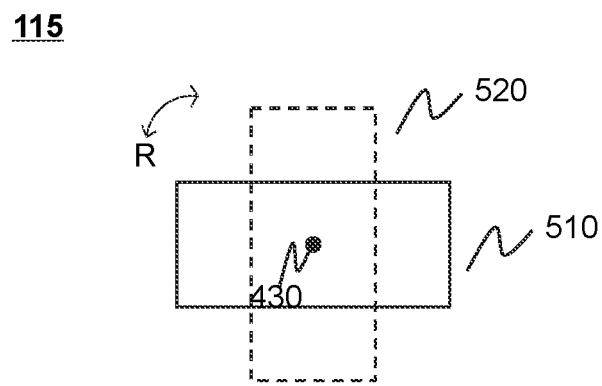
FIG. 5 is a schematic diagram illustrating an exemplary collimator angle according to some embodiments of the present disclosure.

Merely by way of example, FIG. 5 is a schematic diagram illustrating an exemplary collimator angle according to some embodiments of the present disclosure. The MLC 115 shown in FIG. 5 is a cross-section of the MLC 115 vertical to the center line (e.g., coinciding with the center line 430 of the radiation rays 440 shown in FIG. 4) of the MLC 115. The MLC 115 may rotate (e.g., along the direction R in FIG. 5) around its center line (e.g., the center line 430 of the radiation rays 440 shown in FIG. 4).

The location 520 (e.g., represented as dashed lines in FIG. 5) of the MLC 115 may be designated as the initial location. When the MLC 115 rotates, along the direction R, to the location 510 (e.g., represented as solid lines in FIG. 5), an angle between the initial location 520 and the location 510 is 90°. The collimator angle of the MLC 115 at the location 510 is 90°.

In some embodiments, the couch 113 may translate along the X direction, the Y direction, and the Z direction illustrated in FIG. 1. In some embodiments, the couch 113 may rotate around the Y direction, the X direction, or the Z direction illustrated in FIG. 1. The couch location of the couch 113 may indicate at least one of the translation of the couch 113 along the X direction, the translation of the couch 113 along the Y direction, the translation of the couch 113 along the Z direction, the rotation of the couch 113 around the Y direction, the rotation of the couch 113 around the Z direction, and the rotation of the couch 113 around the X direction.

In some embodiments, the MLC 115 may include a plurality of leaf pairs each of which includes two leaves disposed oppositely. In some embodiments, at a target control point, the plurality of leaf pairs may move individually to their respective target leaf locations so that an aperture of a specific shape is formed to establish a therapy beam that approximates the shape of the target. The shape of the aperture of the MLC 115 at the target control point may be referred to as the target segment shape of the MLC 115 at the target control point.

In some embodiments, the target segment shape of the MLC 115 at a target control point may include a target leaf location of each of the plurality of leaf pairs. For example, the target leaf location of a leaf pair may include a location of an opening (e.g., a location of the center point of the opening) formed by the leaf pair and a width of the opening. As another example, a leaf pair may include a first leaf and a second leaf. The target leaf location of the leaf pair may include a first target location of the first leaf and a second target location of the second leaf. In some embodiments, the first target location of the first leaf may be represented as a location of the center point of an end of the first leaf. The end of the first leaf may face the second leaf. The second target location of the second leaf may be represented as a location of the center point of an end of the second leaf. The end of the second leaf may face the first leaf. In some embodiments, each of the plurality of leaf pairs may be numbered. The information regarding the target leaf location of a leaf pair may further include the serial number of the leaf pair.

Figure 6:
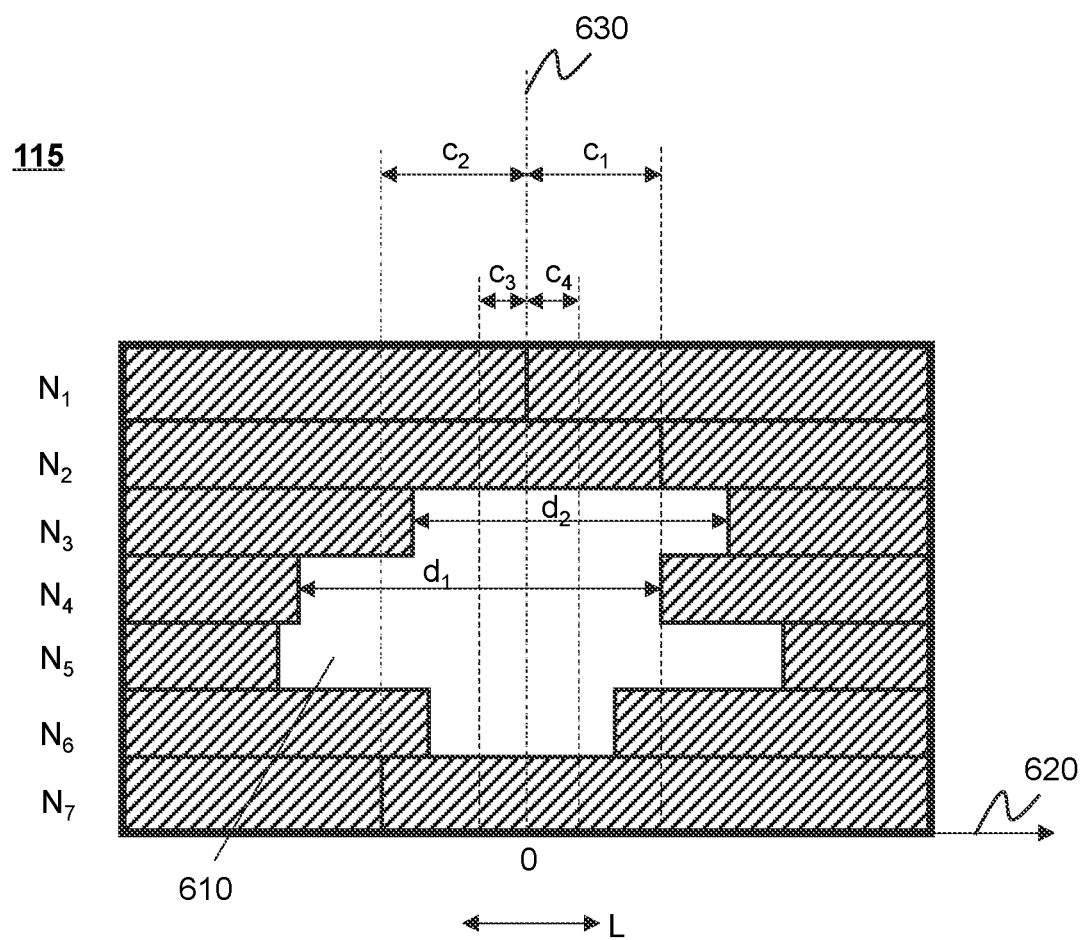
FIG. 6 is a schematic diagram illustrating an exemplary segment shape according to some embodiments of the present disclosure.

For example, FIG. 6 is a schematic diagram illustrating an exemplary segment shape of the MLC 115 according to some embodiments of the present disclosure. The MLC 115 shown in FIG. 6 is a cross-section vertical to the center line (e.g., the center line 430 of the radiation rays 440 shown in FIG. 4) of the MLC 115. As illustrated, the MLC 115 includes 7 leaf pairs (e.g., the shaded blocks in FIG. 6) that can move along the direction L in FIG. 6. The 7 leaf pairs are number as $N_1$-$N_7$, respectively. At a target control point, the leaves of the MLC 115 may form a segment shape 610 (e.g., the white region surrounded by the shaded blocks in FIG. 6).

As shown in FIG. 6, a coordinate system is established based on the MLC 115. The coordinate system includes a coordinate axis 620 along the direction L. The positive direction of the coordinate axis 620 is from the left to the right. The dashed line 630 is designated as the origin of the coordinate system.

In some embodiments, the target leaf location of a leaf pair of the MLC 115 at a target control point may be represented as (N, c, w), wherein N refers to the serial number of the leaf pair, c refers to the location, in, e.g., the coordinate system, of the center point of the opening (e.g., a portion of the segment shape 610) formed by the leaf pair, and w refers to a width of the opening along the direction L. In some embodiments, the width w may be formed by positioning the pair of leaves symmetrically with respect to the center c of the pair of leaves.

For example, the target leaf location of the leaf pair $N_1$ at the target control point may be represented as ($N_1$, 0, 0) because the leaf pair $N_1$ is closed at the origin 630. As another example, the target leaf location of the leaf pair $N_2$ at the target control point may be represented as ($N_2$, $c_1$, 0) because the leaf pair $N_2$ is closed at the location $c_1$ in the coordinate system. The value of $c_1$ is positive. As still another example, the target leaf location of the leaf pair $N_3$ at the target control point may be represented as ($N_3$, $c_4$, $d_2$), wherein $c_4$ refers to the location, in the coordinate system, of the center point of the opening (at portion of the segment shape 610) formed by the leaf pair $N_3$ and is positive, and $d_2$ refers to the width of the opening along the direction L. As still another example, the target leaf location of the leaf pair $N_4$ at the target control point may be represented as ($N_4$, $c_3$, $d_1$), wherein $c_3$ refers to the location, in the coordinate system, of the center point of the opening (at portion of the segment shape 610) formed by the leaf pair $N_4$ and is negative, and $d_1$ refers to the width of the opening along the direction L. As a further example, the target leaf location of the leaf pair $N_7$ at the target control point may be represented as ($N_7$, $c_2$, 0) because the leaf pair $N_7$ is closed at the location $c_2$ in the coordinate system. The value of $c_2$ is negative.

In some embodiments, one of the 7 leaf pairs may include a first leaf and a second leaf. The target leaf location of the leaf pair at the target control point may be represented as (N, $p_1$, $p_2$), wherein $p_1$ refers to the location of the first leaf in the coordinate system, and $p_2$ refers to the location of the second leaf in the coordinate system. The location of the first leaf may be represented as a location of the center point at an end of the first leaf. The end of the first leaf may face the second leaf. The location of the second leaf may be represented as a location of the center point at an end of the second leaf. The end of the second leaf may face the first leaf.

For example, the locations of the leaves of the leaf pair $N_1$ at the target control point may be the same because the leaf pair $N_1$ is closed at the target control point. As another example, a difference between the coordinates, along the axis 620, of the locations of the leaves of the leaf pair $N_3$ at the target control point may be equal to $d_2$.

In some embodiments, the present disclosure provides a training process (e.g., descriptions in connection with FIGS. 7-10) to determine a segment shape estimation model configured to determine a target segment shape corresponding to each of target location combinations at each of a plurality of target control points of a target treatment plan. In some embodiments, the present disclosure also provides a process (e.g., descriptions in connection with FIG. 12) for determining, using a segment shape estimation model, a target segment shape corresponding to each of target location combinations at each of a plurality of target control points of a target treatment plan.

Figure 7:
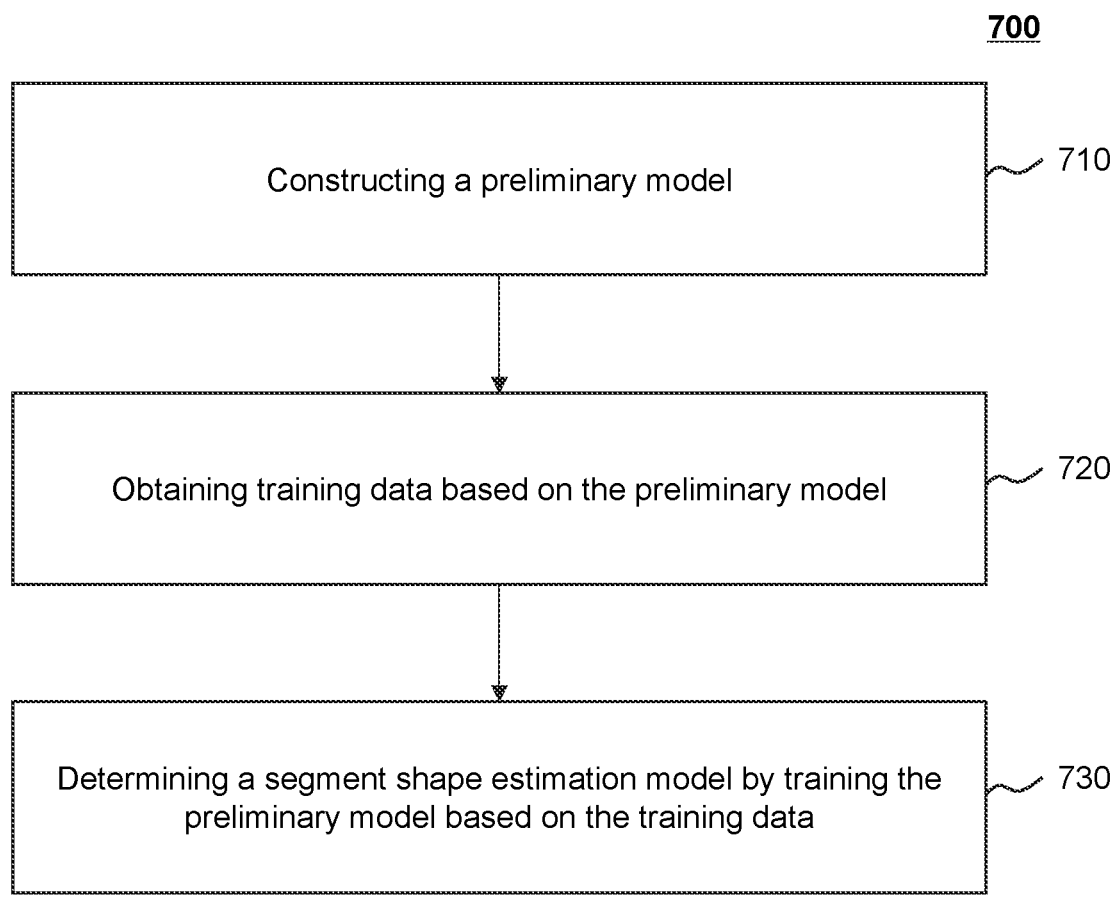
FIG. 7 is a flowchart illustrating an exemplary training process for generating a segment shape estimation model according to some embodiments of the present disclosure.

FIG. 7 is a flowchart illustrating an exemplary training process for generating a segment shape estimation model according to some embodiments of the present disclosure. In some embodiments, one or more operations of the process 700 illustrated in FIG. 7 may be implemented in the medical radiation system 100 illustrated in FIG. 1 or a third party (e.g., an external device). For example, the process 700 illustrated in FIG. 7 may be stored in a storage device (e.g., the storage device 150, and/or the storage 220) of the medical radiation system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules (e.g., the model obtaining module 1120) of the processing device 140 illustrated in FIG. 11). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, a preliminary model may be constructed. In some embodiments, a framework of the preliminary model may be constructed based on a location universal set and a distance universal set so that a resultant segment shape estimation model may be configured to output a plurality of target location combinations within a plurality of discrete candidate location combinations of the location universal set, and a plurality of target segment shapes that correspond to the plurality of target location combinations and is within the distance universal set.

In some embodiments, the location universal set may include a plurality of discrete candidate location combinations. In some embodiments, a plurality of candidate gantry angles, a plurality of candidate couch locations, or a plurality of candidate collimator angles may be obtained. The location universal set may be obtained based on the plurality of candidate gantry angles, the plurality of candidate collimator angles, or the plurality of candidate couch locations. For example, each of the plurality of candidate location combinations in the location universal set may include one of the plurality of candidate gantry angles. As another example, each of the plurality of candidate location combinations in the location universal set may include one of the plurality of candidate gantry angles and one of the plurality of candidate collimator angles. As another example, each of the plurality of candidate location combinations in the location universal set may include a combination of one from each of the plurality of candidate gantry angles, the plurality of candidate collimator angles, and the plurality of candidate couch locations.

In some embodiments, the type of elements in the location universal set may be determined based on the type of treatment plans the segment shape estimation model is desired to be applied for. For example, if a segment shape estimation model configured to determine segment shapes corresponding to gantry-collimator angle combinations needs to be generated, the location universal set may include a combination of a plurality of candidate gantry angles and a plurality of candidate collimator angles.

Taking gantry-collimator angle combinations as an example, a range of candidate gantry angles and a range of candidate collimator angles may be obtained. A plurality of discrete candidate gantry angles and a plurality of discrete candidate collimator angles may be obtained from the range of candidate gantry angles and the range of candidate collimator angles, respectively. For example, the plurality of discrete candidate gantry angles may be selected, based on a first angle resolution, from the range of candidate gantry angles. A difference between any two neighboring candidate gantry angles of the plurality of candidate gantry angles may be equal to the first angle resolution. As another example, the plurality of discrete candidate collimator angles may be selected, based on a second angle resolution, from the range of candidate collimator angles. A difference between any two neighboring candidate collimator angles of the plurality of candidate collimator angles may be equal to the second angle resolution. The first angle resolution and the second angle resolution may be the same or different.

Merely by way of example, the range of candidate gantry angles and the range of candidate collimator angles may be set as 360°. A plurality of discrete candidate gantry angles, each 0.5° (the first angle resolution) apart, may be selected from the range of candidate gantry angles. For example, the plurality of candidate gantry angles may be represented as $\{0°, 0.5°, 1.0°, \ldots, 359.5°\}$. A plurality of discrete candidate collimator angles, each 0.5° (the second angle resolution) apart, may be selected from the range of candidate collimator angles. For example, the plurality of candidate collimator angles may be represented as $\{0°, 0.5°, 1.0°, \ldots, 359.5°\}$. The location universal set may include 720*720 gantry-collimator angle combinations based on the 720 candidate gantry angles and the 720 candidate collimator angles.

In some embodiments, larger ranges of candidate gantry angles and the range of candidate collimator angles, and smaller values of the first and the second angle resolutions (e.g., higher first and second angle resolutions) may increase the output quantity of the resultant segment shape estimation model, thereby increasing the application and the precision of the resultant segment shape estimation model. For example, if the range of the candidate gantry angles in the location universal set is less than 360°, the resultant segment shape estimation model may not be applied to a single arc treatment plan and a multi-arc treatment plan. As another example, if the first angle resolution in the location universal set is 5°, and gantry angles in a target treatment plan are accurate to 0.5°, the target segment shapes determined for the target treatment plan using the resultant segment shape estimation model may be inaccurate. As still another example, if the first angle resolution in the location universal set is 0.5°, the resultant segment shape estimation model may accurately determine target segment shapes for a target treatment plan in which gantry angles are accurate to, e.g., 0.5°, 1°, 2°, 5°, etc.

In some embodiments, the distance universal set may include a plurality of discrete candidate leaf locations. Assuming that each of the plurality of candidate leaf locations includes a candidate opening location and a candidate opening width, to obtain the distance universal set, a plurality of candidate opening locations and a plurality of candidate opening widths may be obtained. Each of the plurality of candidate leaf locations may include one of the plurality of candidate opening locations and one of the plurality of candidate opening widths. In some embodiments, a range of candidate opening locations and a range of candidate opening widths may be obtained. A plurality of candidate opening locations and a plurality of candidate opening widths may be obtained from the range of candidate opening locations and the range of candidate opening widths, respectively. For example, the plurality of candidate opening locations may be selected, based on a first distance resolution, from the range of candidate opening locations. A difference between any two neighboring candidate opening locations of the plurality of candidate opening locations may be equal to the first distance resolution. As another example, the plurality of candidate opening widths may be selected, based on a second distance resolution, from the range of candidate opening widths. A difference between any two neighboring candidate opening widths of the plurality of candidate opening widths may be equal to the second distance resolution.

For example, the range of candidate opening locations may be set as −200 mm to +200 mm, and the range of candidate opening widths may be set as 0-150 mm. A plurality of discrete candidate opening locations, each 0.5 mm (the first distance resolution) apart, may be selected from the range of candidate opening locations. For example, the plurality of candidate opening locations may be represented as $\{-200, -199.5, \ldots 0, 0.5, \ldots, 200\}$. A plurality of discrete candidate opening widths, each 0.5 mm (the second distance resolution) apart, may be selected from the range of candidate opening widths. For example, the plurality of candidate opening widths may be represented as $\{0, 0.5, 1.0, \ldots 150\}$.

In some embodiments, larger ranges of candidate opening locations and the range of candidate opening widths, and smaller values of the first and the second distance resolutions (e.g., higher first and second distance resolutions) may increase the application and the precision of the resultant segment shape estimation model. For example, if the ranges of the candidate opening locations and the candidate opening widths in the distance universal set is relatively narrow, the resultant segment shape estimation model may not be applied to a treatment plan for treating a relatively large lesion. As another example, if the first and the second distance resolutions in the distance universal set is relatively high, target segment shapes determined for a target treatment plan using the resultant segment shape estimation model may be more accurate to approximate the shape of a target.

In some embodiments, the preliminary model may be further constructed based on a count of leaf pairs so that the resultant segment shape estimation model may be configured to output a leaf location of each leaf pair corresponding to the plurality of candidate location combinations, and applied for an MLC with the same number (or count) leaf pairs. For example, the preliminary model may be constructed based on a count of leaf pairs equal to 60 and a location universal set including 720*720 candidate location combinations, so that the resultant segment shape estimation model is applied for a type of MLC with 60 leaf pairs, and configured to output 720*720*60, 3,1104,000 in total, leaf locations corresponding to the 720*720 candidate location combinations.

In some embodiments, a framework of the preliminary model may be constructed based on the discrete finite location universal set and the discrete finite distance universal set so that a resultant segment shape estimation model may be configured to estimate a plurality of target location combinations and corresponding target segment shapes from the location universal set and the distance universal set. The space of the gantry angles, the collimator angles, the couch positions, the leaf positions are "discretized" (like 0.5 degree or 1 mm) in the location universal set and the distance universal set so that the overall set of the location universal set and the distance universal set is large but still a finite set, which makes the prediction of the target location combinations and the target segment shapes using the segment shape estimation model have a controllable operation amount, an efficient operation speed, and an accurate operation result. For example, the location universal set may include 720*720 gantry-collimator angles that are a combination of 720 discrete candidate gantry angles {0°, 0.5°, 1.0°, ..., 359.5°} and 720 discrete candidate collimator angles {0°, 0.5°, 1.0°, ..., 359.5°}. The distance universal set may include 801*301 leaf locations that are a combination of 801 discrete candidate opening locations {−200, −199.5, ... 0, 0.5, ..., 200} and 301 discrete candidate opening widths {0, 0.5, 1.0, ... 150}. The overall set of the location universal set and the distance universal set is large but still a finite set.

In 720, training data may be obtained based on the preliminary model. In some embodiments, the training data may include a plurality of training sets. In some embodiments, one of the plurality of training sets may be obtained based on information of a historical treatment plan previously generated for a sample (e.g., a lesion of a patient, also referred to as a sample). Details related to obtaining the training data may be found elsewhere in the present disclosure (e.g., descriptions in connection with FIG. 8).

In 730, a segment shape estimation model may be determined by training the preliminary model based on the training data.

In some embodiments, the training process may be an offline process, during which a database of training data with ground truth measurements is assembled. For instance, a database of previously generated treatment plans for different patients may be constructed. In this database, the training data may be represented by a number (or count) of features. The training process may then learn or train a mapping between the features and the ground truth values by achieving a best fit between predictions and ground truth values over a portion of or the entire training database.

In the training process, the training data (including training inputs and the corresponding known outputs) may be input into the constructed preliminary model so that the constructed preliminary model may learn how to provide an output for new input data by generalizing the information learned in the training process from the training data.

In some embodiments, the preliminary model may include a plurality of parameters. The values of the parameters in the preliminary model may be updated by performing an iterative backpropagation training procedure, e.g., a stochastic gradient descent backpropagation training technique, to determine the segment shape estimation model. That is, the preliminary model may backpropagate the error determined for the output in the preliminary model in order to adjust the parameters of the preliminary model.

In some embodiments, the segment shape estimation model may be a machine learning model. In some embodiments, the segment shape estimation model may be a deep learning model. In some embodiments, the segment shape estimation model may be a deep convolution—deconvolution (e.g., an encoder—decoder) network, such as, U-shaped convolutional neural network (U-Net), V-shaped convolutional neural network (V-Net), residual network (Res-Net) or residual dense network (Red-Net), or the like.

Figure 10:
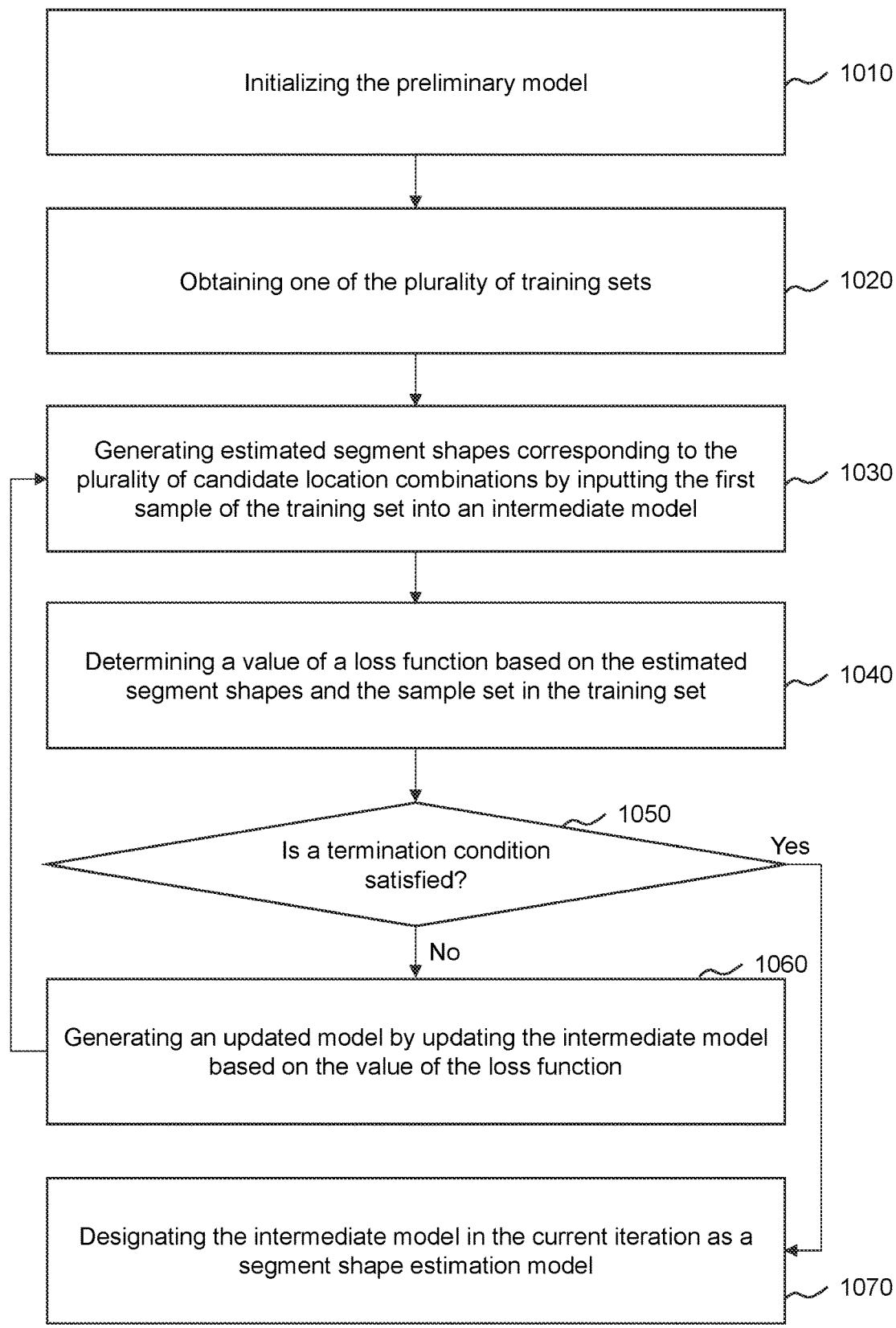
FIG. 10 is a flowchart illustrating an exemplary process for determining a segment shape estimation model according to some embodiments of the present disclosure.

Details related to a training process for determining the segment shape estimation model may be found elsewhere in the present disclosure (e.g., descriptions in connection with FIG. 10).

In some embodiments, as more data is collected, the training database containing the training data may grow in size. The updated database may then be used to re-train the segment shape estimation model, e.g., periodically or aperiodically. The new samples in the training database may be from unseen treatment plans (e.g., treatment plans that have not been used for either training or prediction in the past) or from treatment plans which were used for prediction in the past, but now have been updated.

Figure 11:
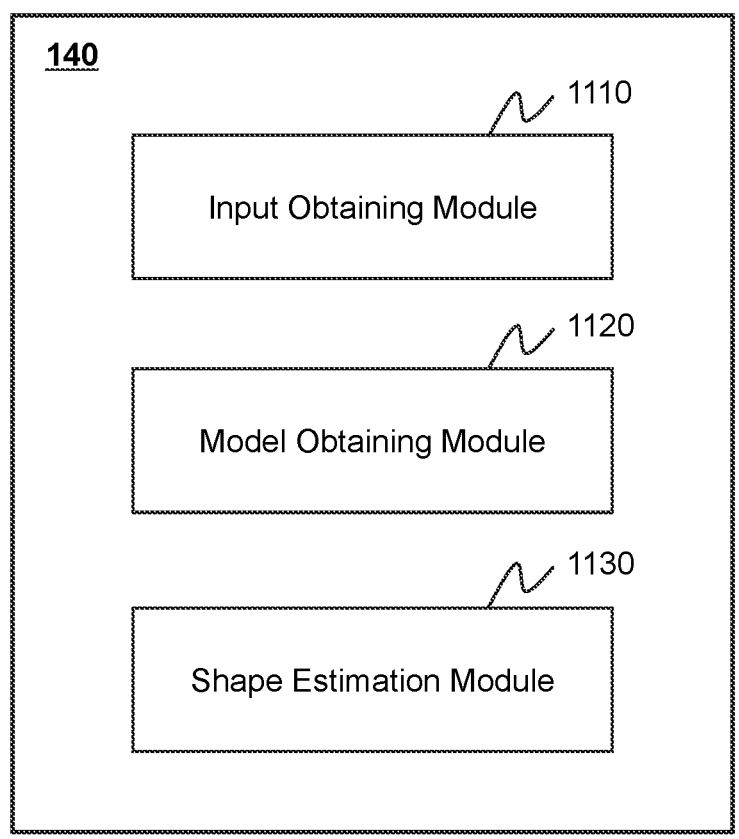
FIG. 11 is a block diagram illustrating an exemplary processing device according to some embodiments of the present disclosure.

In some embodiments, the segment shape estimation model may be determined and/or updated by the medical radiation system 100 (e.g., the processing device 140, the model obtaining module 1120 of the processing device 140 in FIG. 11) or a third party (e.g., an external device). In some embodiments, the medical radiation system 100 may determine and/or update the segment shape estimation model offline and store the segment shape estimation model in the storage device (e.g., the storage device 150, the storage 220, or the storage 390). In some embodiments, the segment shape estimation model may be determined and/or updated (or maintained) by, e.g., the manufacturer of the radiation device 110 or a vendor. For instance, the manufacturer or the vendor may load the segment shape estimation model into the medical radiation system 100, or a portion thereof (e.g., the processing device 140), before or during the installation of the radiation device 110 and/or the processing device 140, and maintain or update the segment shape estimation model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 120. The program may include a new segment shape estimation model or a portion of a model that substitute or supplement a corresponding portion of the segment shape estimation model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 8:
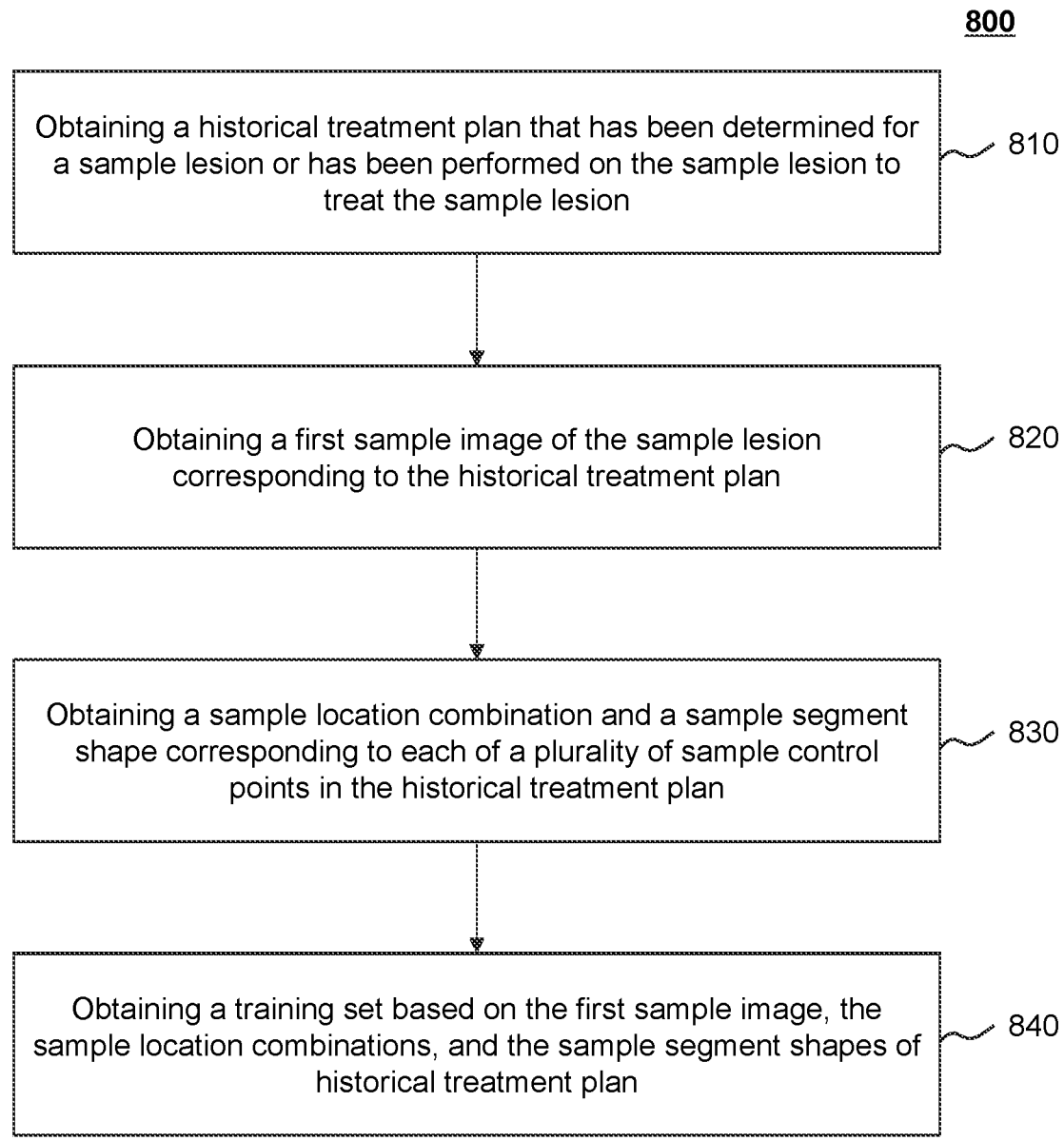
FIG. 8 is a flowchart illustrating an exemplary process for obtaining training data according to some embodiments of the present disclosure.

FIG. 8 is a flowchart illustrating an exemplary process for obtaining training data according to some embodiments of the present disclosure. In some embodiments, one or more operations of the process 800 illustrated in FIG. 8 may be implemented in the medical radiation system 100 illustrated in FIG. 1 or a third party (e.g., an external device). For example, the process 800 illustrated in FIG. 8 may be stored in a storage device (e.g., the storage device 150, and/or the storage 220) of the medical radiation system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules (e.g., the model obtaining module 1120) of the processing device 140 illustrated in FIG. 11). The operations of the illustrated process presented below are intended to be illustrative. In some embodiments, the process 800 may be accomplished with one or more additional operations not described, and/or without one or more of the operations discussed. Additionally, the order in which the operations of the process 800 as illustrated in FIG. 8 and described below is not intended to be limiting. In some embodiments, the operation 720 of the process 700 in FIG. 7 may be performed based on the process 800.

In some embodiments, the training data may include a plurality of training sets. One of the plurality of training sets may be obtained based on the process 900. In some embodiments, the rest of the plurality of training sets may also be obtained based on the process 800.

In 810, a historical treatment plan previously generated for a sample (e.g., a sample) lesion may be obtained. In some embodiments, the historical treatment plan may be obtained from a storage device (e.g., the storage device 150, the storage 220, the storage 390, etc.). In some embodiments, the type of the historical treatment plan may correspond to the preliminary model. For example, the number (or count) of leaf pairs of an MLC corresponding to the historical treatment plan may be equal to that corresponding to the preliminary model. As another example, if the location universal set used to construct the preliminary model includes a plurality of gantry-collimator angle combinations, location combinations (also referred to as sample location combinations) in the historical treatment plan may be gantry-collimator angle combinations. As still another example, the range of the sample location combinations in the historical treatment plan may be within the range of the candidate location combinations in the location universal set used to construct the preliminary model.

In 820, one or more first sample images of the sample corresponding to the historical treatment plan may be obtained. In some embodiments, the historical treatment plan was previously generated based on the one or more first sample images of the sample. In some embodiments, the one or more first sample images may include identification of the sample. For example, the outline of the sample may be remarked in the one or more first sample images. In some embodiments, the identification of the sample may be performed or modified manually by a user (e.g., a doctor). In some embodiments, the identification of the sample may be performed automatically using an image segmentation algorithm or an image segmentation model.

In 830, a sample location combination and a sample segment shape corresponding to each of a plurality of sample control points in the historical treatment plan may be obtained.

In 840, the training set may be obtained based on the one or more first sample images, the sample location combinations, and the sample segment shapes of the historical treatment plan. In some embodiments, the sample location combination and the sample segment shape corresponding to each of a plurality of sample control points may be processed based on the location universal set and the distance universal set to obtain the training set. Details related to obtaining the training data may be found elsewhere in the present disclosure (e.g., descriptions in connection with FIG. 9).

In some embodiments, one or more second sample images of normal tissue surrounding the sample, one or more third images of the sample, and sample radiation information of the historical treatment plan may be obtained. The training set may be obtained by further including the one or more second sample images, the one or more third sample images, and/or the sample radiation information. In some embodiments, the one or more first sample images of the sample may be acquired by scanning the sample. For example, a first sample image may include a single modality image and/or a multi-modality image. The single modality image may include, for example, a magnetic resonance (MR) image, a CT image, a PET image, an SPECT image, an ultrasound image, an X-ray image, or the like. The multi-modality image may include, for example, a computed tomography-magnetic resonance imaging (MRI-CT) system, a PET-MR image, an SPECT-MR image, a DSA-MR image, a PET-CT image, a SPECT-CT image, etc. In some embodiments, a first sample image may be a reconstructed image, such as a three-dimensional (3D) rendered image, a multi-planar reconstruction (MPR) image, a curved planar reformation (CPR) image, or the like.

In some embodiments, a second sample image of normal tissue surrounding the sample may be a mask image of the surrounding normal tissue separated from at least one of the one or more first sample images. In some embodiments, a third sample image of the sample may be a mask image of the sample separated from at least one of the one or more first sample images. In some embodiments, the sample radiation information may include at least one of a sample output dose, a sample dose output rate, a sample dose distribution in the sample, a sample dose output per pulse, the acceptable dose to the normal tissue surrounding the sample, the minimum dose to the sample, or the like, or any combination thereof. In some embodiments, the sample radiation information may be determined based on the one or more first sample images, the one or more second sample images, and/or the one or more third sample images. In some embodiments, the sample radiation information may be determined using a dose prediction model.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 9:
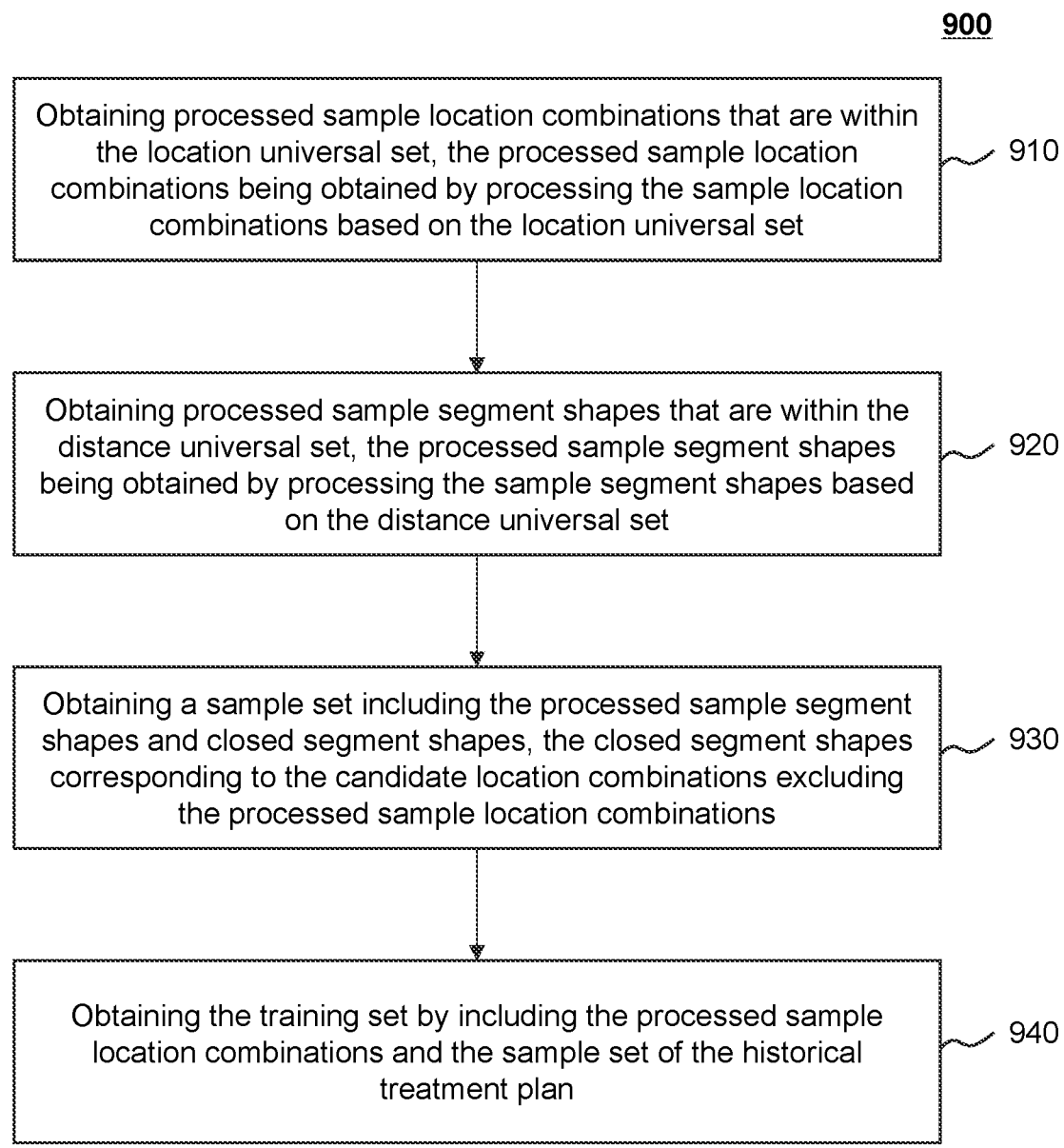
FIG. 9 is a flowchart illustrating an exemplary process for obtaining training data according to some embodiments of the present disclosure.

FIG. 9 is a flowchart illustrating an exemplary process for obtaining training data according to some embodiments of the present disclosure. In some embodiments, one or more operations of the process 900 illustrated in FIG. 9 may be implemented in the medical radiation system 100 illustrated in FIG. 1 or a third party (e.g., an external device). For example, the process 900 illustrated in FIG. 9 may be stored in a storage device (e.g., the storage device 150, and/or the storage 220) of the medical radiation system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules (e.g., the model obtaining module 1120) of the processing device 140 illustrated in FIG. 11). The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting. In some embodiments, the operation 840 of the process 800 in FIG. 8 may be performed based on the process 900.

In 910, processed sample location combinations that are within the location universal set may be obtained. In some embodiments, the processed sample location combinations may be obtained by processing, based on the location universal set, the sample location combinations of the historical treatment plan obtained in operation 830.

Merely by way of example, the preliminary model may be constructed based on a location universal set including 720*720 gantry-collimator angle combinations. The 720*720 gantry-collimator angle combinations may be determined based on 720 candidate gantry angles {0°, 0.5°, 1.0°, ..., 359.5°} and 720 candidate collimator angles {0°, 0.5°, 1.0°, ..., 359.5°}. The sample gantry angle and sample collimator angle of a sample gantry-collimator angle combination may be modeled to their respective nearest 0.5° point that includes the sample gantry angle and sample collimator angle. For example, a sample gantry angle 40.1° may be processed and set to be 40°.

In 920, processed sample segment shapes that are within the distance universal set may be obtained. In some embodiments, the processed sample segment shapes may be obtained by processing, based on the distance universal set, the sample segment shapes of the historical treatment plan obtained in operation 830. Merely by way of example, the preliminary model may be constructed based on a distance universal set including candidate opening locations {−200, −199.5, ... 0, 0.5, ..., 200} and candidate opening widths {0, 0.5, 1.0, ... 150}. The sample opening location and the sample opening width of a sample segment shape may be modeled to their respective nearest 0.5 mm point that includes the sample opening location and sample opening width. For example, a sample opening width 10.6 mm may be processed and set to be 10.5 mm.

In 930, a sample set including the processed sample segment shapes and closed segment shapes may be obtained. The closed segment shapes may correspond to the candidate location combinations excluding the processed sample location combinations. In some embodiments, a closed segment shape of an MLC may indicate that all leaf pairs of the MLC are closed. In the sample set, each of the plurality of candidate location combinations may have a corresponding segment shape. In some embodiments, there may be 180-240 sample control points in the historical treatment plan. If the location universal set includes 720*720 candidate location combinations, most segment shapes in the sample set may be closed segment shapes. Due to the closed segment shapes, the sample set may be deemed as having sparsity.

In 940, the training set may be obtained by including the processed sample location combinations and the sample set of the historical treatment plan.

In some embodiments, at least one of the operations 910-930 may be performed outside the preliminary model. In some embodiments, at least one of the operations 910-930 may be performed by the preliminary model. For example, the sample location combinations or the sample segment shapes may be input into the preliminary model. The processed sample segment shapes or the processed sample location combinations may be obtained by processing, by the preliminary model, the sample segment shapes or the sample location combinations. Alternatively or additionally, the preliminary model may obtain the sample set based on the processed sample segment shapes and the processed sample location combinations.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 10 is a flowchart illustrating an exemplary process for determining a segment shape estimation model according to some embodiments of the present disclosure. In some embodiments, one or more operations of the process 1000 illustrated in FIG. 10 may be implemented in the medical radiation system 100 illustrated in FIG. 1 or a third party (e.g., an external device). For example, the process 1000 illustrated in FIG. 10 may be stored in a storage device (e.g., the storage device 150, and/or the storage 220) of the medical radiation system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules (e.g., the model obtaining module 1120) of the processing device 140 illustrated in FIG. 11). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting. In some embodiments, the operation 730 of the process 700 in FIG. 7 may be performed based on the process 1000.

In 1010, the preliminary model may be initialized. In some embodiments, the constructed preliminary model may include a plurality of parameters. Each of the plurality of parameters may be assigned an initial value. The initialized preliminary model may be trained using the training data in order to determine trained values of the plurality of parameters. That is, the initialized preliminary model may be trained in order to update the plurality of the parameters from the initial values to trained values, so as to generate the segment shape estimation model.

In some embodiments, a segment shape estimation model may be determined by updating the initialized preliminary model using an iteration process including a plurality of iterations. At least one of the plurality of iterations of the iteration process may include operations 1020-1060.

In 1020, one of the plurality of training sets may be obtained. In some embodiments, a set of features may be extracted from the training set. In some embodiments, depending on the source and type of data in the training set, the extracted features may be binary, numerical, categorical, ordinal, binomial, interval, text-based, or combinations thereof.

In addition to the above described features, one or more derived features may also be determined from the extracted features. For example, the derived feature(s) may be represented as linear or non-linear combinations of the extracted features.

In some embodiments, the feature extraction from the training set may be fully automated, semi-automated, manual, or a combination thereof. For example, in a fully-automated feature extraction approach, one or more image processing algorithms may first detect a region corresponding to the sample in the one or more first sample images and then extract the features from the detected region. Under a semi-automated approach, some of the features may be extracted automatically, while others and/or the automatically extracted features may be annotated, edited, or corrected by a user. Under a manual approach, the features may be annotated or measured by a user.

In some embodiments, the preliminary model may learn features as part of the training. For example, the preliminary model may be a deep learning model. Deep learning (e.g., deep structured learning, hierarchical learning, or deep machine learning) may model high-level abstractions in data by using multiple processing layers with structures composed of multiple non-linear transformations, where the input data features are not engineered explicitly. A deep neural network may process the input via multiple layers of feature extraction to produce features used to derive outputs. The machine training may be unsupervised in learning the features to use and how to classify given a training sample (e.g., a feature vector). Using deep learning, the input features needed for the machine learning are not engineered by the user explicitly.

In 1030, estimated segment shapes corresponding to the plurality of candidate location combinations in the location universal set may be generated by inputting the one or more first sample images of the training set into an intermediate model. In some embodiments, the one or more second sample images, the one or more third sample images, and/or the sample radiation information in the training set may be further input into the intermediate model. In some embodiments, the intermediate model may be the initialized preliminary model in a first iteration of the plurality of iterations of the iteration process or a previously updated model generated in a previous iteration in the iteration process. In some embodiments, data in the training set input into the preliminary model may be in the form of the extracted features illustrated in operation 1020.

In some embodiments, according to the input, the intermediate model may select some of the plurality of candidate location combinations and estimate, from the distance universal set, corresponding segment shapes having real shapes. The segment shapes of rest of the plurality of candidate location combinations may be determined as closed shapes.

The estimated segment shapes output by the intermediate model may include the segment shapes having real shapes and corresponding to the selected candidate location combinations and the closed segment shapes corresponding to the rest of the plurality of candidate location combinations.

In 1040, a value of a loss function may be determined based on the estimated segment shapes and the sample set in the training set.

In some embodiments, the value of the loss function (also referred to as a loss) may be determined by comparing the processed sample segment shapes (e.g., segment shapes determined by a treatment planning system (TPS)) and the estimated segment shapes corresponding to the candidate location combinations. In some embodiments, the value of the loss function may be determined by comparing all segment shapes in the sample set and all output estimated segment shapes.

In some embodiments, when an estimated segment shape is compared with a corresponding segment shape in the sample set, each leaf location $(c_P, w_P)$ of the estimated segment shape may be compared with the corresponding leaf location $(c_T, w_T)$ of the segment shape in the sample set. In some embodiments, a loss between $(c_P, w_P)$ and $(c_T, w_T)$ may be determined based on the disjoint (i.e., non-overlapping) open area defined by $(c_P, w_P)$ and $(c_T, w_T)$. For example, a large loss may be introduced if $(c_T, w_T)$ indicates a closed leaf pair but $(c_P, w_P)$ indicates an opened leaf pair. As another example, if both $(c_P, w_P)$ and $(c_T, w_T)$ indicate a closed leaf pair, but closed at different positions, namely $w_P = W_T = 0$, $(c_P, w_P)$ and $(c_T, w_T)$ may be considered equivalent and no loss may be introduced.

In some embodiments, a loss function appropriate for the sparsity of the sample set may be selected to determine a loss between the estimated segment shapes and the sample set.

In some embodiments, estimated radiation information may be determined based on the estimated segment shapes. In some embodiments, the estimated radiation information may correspond to each of the plurality of sample control points. In some embodiments, the estimated radiation information may include at least one of an estimated output dose, an estimated dose output rate, an estimated dose distribution in the sample, an estimated dose output per pulse, or the like, or any combination thereof. In some embodiments, the estimated radiation information may be determined based on the estimated segment shapes using a treatment planning algorithm or model. In some embodiments, the estimated radiation information may be compared with the sample radiation information (e.g., radiation information determined by a treatment planning system (TPS)) in the training set. A loss may be determined based on the comparison. The loss may be backpropagated back into the training process to update the intermediate model.

In 1050, a determination as to whether a termination condition is satisfied may be determined. In some embodiments, the termination condition may relate to at least one of the value of the loss function or a count of iterations of the iteration process that have been performed.

In some embodiments, an exemplary termination condition may be that the value of the loss function is less than a threshold value. Other exemplary termination conditions may include that a maximum number (or count) of iterations has been performed, and/or a difference between the values of the loss function obtained in a previous iteration and the current iteration (or among the values of the loss function within a certain number or count of successive iterations) is less than a certain threshold.

In response to determining that the termination condition is not satisfied in 1050, the process 1000 may proceed to 1060, and further repeat operations 1020-1050 until the termination condition is satisfied. In response to determining that the termination condition is satisfied in 1050, the iterative process may terminate. The process 1000 may proceed to 1070 in which the intermediate model in the current iteration may be stored and/or output as the segment shape estimation model.

In 1060, an updated model may be generated by updating the intermediate model based on the value of the loss function.

In the training process, the training data may be input into the intermediate model so that the intermediate model may learn how to determine, based on new input data (e.g., the geometry of a lesion and/or surrounding tissue, and/or does information), target location combinations from the location universal set and corresponding target segment shapes from the distance universal set.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

FIG. 11 is a schematic diagram illustrating an exemplary processing device 140 according to some embodiments of the present disclosure. The processing device 140 may include an input obtaining module 1110, a model obtaining module 1120, and a shape estimation module 1130.

The input obtaining module 1110 may obtain input data relating to a target treatment plan for performing radiotherapy on a target using a radiation device. In some embodiments, the target treatment plan may include a plurality of target control points.

In some embodiments, the input data may include one or more first target images of the target. In some embodiments, the input data may further include one or more second target images of normal tissue surrounding the target, one or more third target images of the target, and/or target radiation information of the target treatment plan. In some embodiments, a first target image may be acquired by scanning the target using an imaging device (e.g., the imaging device 160 of the medical radiation system 100). For example, the first target image may include a single modality image and/or a multi-modality image. The single modality image may include, for example, a magnetic resonance (MR) image, a CT image, a PET image, an SPECT image, an ultrasound image, an X-ray image, or the like. The multi-modality image may include, for example, a computed tomography-magnetic resonance imaging (MRI-CT) system, a PET-MR image, an SPECT-MR image, a DSA-MR image, a PET-CT image, a SPECT-CT image, etc. In some embodiments, a first target image may be a reconstructed image, such as a three-dimensional (3D) rendered image, a multi-planar reconstruction (MPR) image, a curved planar reformation (CPR) image, or the like.

In some embodiments, a second target image may be a mask image of the surrounding normal tissue separated from at least one of the one or more first target images. In some embodiments, a third target image may be a mask image of the target separated from at least one of the one or more first target images. In some embodiments, the target radiation information may include an output dose, a dose output rate, a radiation output per pulse, a dose distribution in the target, the acceptable dose to the normal tissue surrounding the target, the minimum dose to the target, or the like, or any combination thereof. In some embodiments, the target radiation information may be predicted based on the one or more first target images, the one or more target sample images, and/or the one or more third target images. In some embodiments, the target radiation information may be predicted using a dose prediction model.

In some embodiments, the type of the target treatment plan may correspond to the segment shape estimation model. For example, the number (or count) of leaf pairs of an MLC corresponding to the target treatment plan may be equal to that corresponding to the segment shape estimation model. As another example, if the location universal set used to determine the segment shape estimation model includes a plurality of gantry-collimator angle combinations, target location combinations in the target treatment plan may be gantry-collimator angle combinations. As still another example, the range of the target location combinations in the target treatment plan may be within the range of the candidate location combinations in the location universal set used to determine the segment shape estimation model.

The model obtaining module 1120 may obtain a segment shape estimation model. In some embodiments, the segment shape estimation model may be a machine learning model. In some embodiments, the segment shape estimation model may be a deep learning model. In some embodiments, the segment shape estimation model may be a deep convolution—deconvolution (e.g., an encoder—decoder) network, such as, U-shaped convolutional neural network (U-Net), V-shaped convolutional neural network (V-Net), residual network (Res-Net) or residual dense network (Red-Net), or the like.

In some embodiments, the model obtaining module 1120 may be configured to determine the segment shape estimation model by iteratively training a preliminary model based on training data.

The shape estimation module 1130 may estimate, based on the segment shape estimation model and the input data, a plurality of target location combinations of the target treatment plan and a plurality of target segment shapes of a collimator of the radiation device. Each of the plurality of target segment shapes may correspond to one of the plurality of target location combinations.

In some embodiments, according to the input data, the segment shape estimation model may select, as the plurality of target location combinations, some of the candidate location combinations in the location universal set and estimate, from the distance universal set, segment shapes each of which approximates the shape of the target at one of the target location combinations. In some embodiments, the segment shape estimation model may output a plurality of candidate segment shapes of which the segment shapes corresponding to the target location combinations have real shapes and the rest segment shapes are closed shapes. The output candidate segment shapes having real shapes may be designated as the target segment shapes. The candidate location combinations corresponding to the segment shapes may be designated as the target location combinations. In some embodiments, the segment shape estimation model may directly output a plurality of target locations combinations and corresponding target segment shapes.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 4). The storage module may be configured to store data generated during any process performed by any component of in the processing device 140. As another example, each of components of the processing device 140 may include a storage device. Additionally or alternatively, the components of the processing device 140 may share a common storage device.

Figure 12:
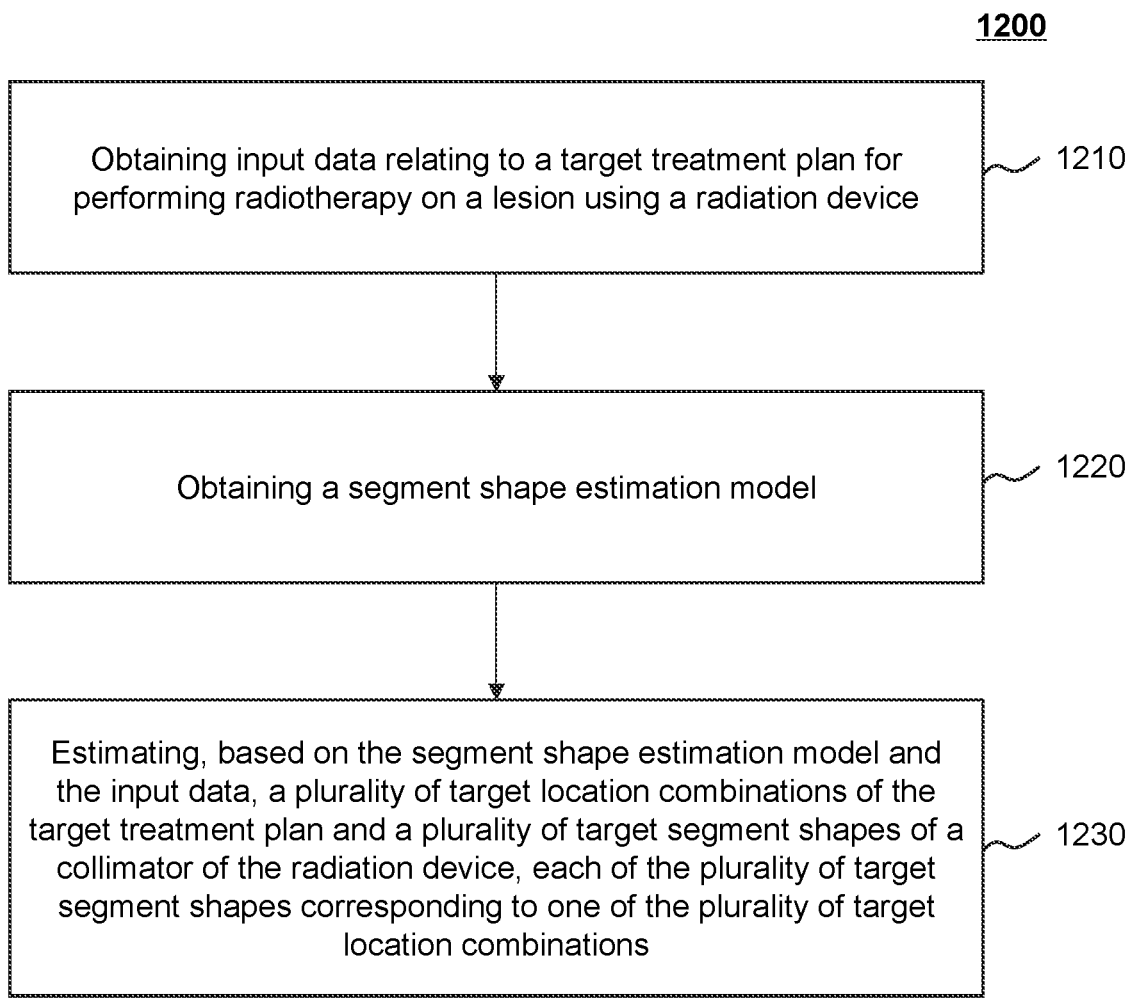
FIG. 12 is a flowchart illustrating an exemplary process for estimating segment shapes of an MLC based on a segment shape estimation model according to some embodiments of the present disclosure.

FIG. 12 is a flowchart illustrating an exemplary process for estimating segment shapes of an MLC based on a segment shape estimation model according to some embodiments of the present disclosure. In some embodiments, one or more operations of the process 1200 illustrated in FIG. 12 may be implemented in the medical radiation system 100 illustrated in FIG. 1. For example, the process 1200 illustrated in FIG. 12 may be stored in a storage device (e.g., the storage device 150, and/or the storage 220) of the medical radiation system 100 in the form of instructions, and invoked and/or executed by the processing device 140 (e.g., the processor 210 of the computing device 200 as illustrated in FIG. 2, the CPU 340 of the mobile device 300 as illustrated in FIG. 3, or one or more modules of the processing device 140 illustrated in FIG. 11). The operations of the illustrated process presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1210, the processing device 140 (e.g., the input obtaining module 1110) may obtain input data relating to a target treatment plan for performing radiotherapy on a target using a radiation device. In some embodiments, the target treatment plan may include a plurality of target control points.

In some embodiments, the input data may include one or more first target images of the target. In some embodiments, the input data may further include one or more second target images of normal tissue surrounding the target, one or more third target images of the target, and/or target radiation information of the target treatment plan. In some embodiments, a first target image may be acquired by scanning the target using an imaging device (e.g., the imaging device 160 of the medical radiation system 100). For example, the first target image may include a single modality image and/or a multi-modality image. The single modality image may include, for example, a magnetic resonance (MR) image, a CT image, a PET image, an SPECT image, an ultrasound image, an X-ray image, or the like. The multi-modality image may include, for example, a computed tomography-magnetic resonance imaging (MRI-CT) system, a PET-MR image, an SPECT-MR image, a DSA-MR image, a PET-CT image, a SPECT-CT image, etc. In some embodiments, a first target image may be a reconstructed image, such as a three-dimensional (3D) rendered image, a multi-planar reconstruction (MPR) image, a curved planar reformation (CPR) image, or the like.

In some embodiments, a second target image may be a mask image of the surrounding normal tissue separated from at least one of the one or more first target images. In some embodiments, a third target image may be a mask image of the target separated from at least one of the one or more first target images. In some embodiments, the target radiation information may include an output dose, an output rate, a radiation output per pulse, a dose distribution in the target, the acceptable dose to the normal tissue surrounding the target, the minimum dose to the target, or the like, or any combination thereof. In some embodiments, the target radiation information may be predicted based on the one or more first target images, the one or more target sample images, and/or the one or more third target images. In some embodiments, the target radiation information may be predicted using a dose prediction model.

In some embodiments, the type of the target treatment plan may correspond to the segment shape estimation model. For example, the number (or count) of leaf pairs of an MLC corresponding to the target treatment plan may be equal to that corresponding to the segment shape estimation model. As another example, if the location universal set used to determine the segment shape estimation model includes a plurality of gantry-collimator angle combinations, target location combinations in the target treatment plan may be gantry-collimator angle combinations. As still another example, the range of the target location combinations in the target treatment plan may be within the range of the candidate location combinations in the location universal set used to determine the segment shape estimation model.

In 1220, the processing device 140 (e.g., the model obtaining module 1120) may obtain a segment shape estimation model. In some embodiments, the segment shape estimation model may be a machine learning model. In some embodiments, the segment shape estimation model may be a deep learning model. In some embodiments, the segment shape estimation model may be a deep convolution—deconvolution (e.g., an encoder—decoder) network, such as, U-shaped convolutional neural network (U-Net), V-shaped convolutional neural network (V-Net), residual network (Res-Net) or residual dense network (Red-Net), or the like.

In some embodiments, the segment shape estimation model may be provided based on the processes 700-1000. In some embodiments, the segment shape estimation model may be regarded as having learned how to determine, based on new input data (e.g., the geometry of a lesion and/or surrounding tissue, and/or does information), target location combinations from the location universal set and corresponding target segment shapes from the distance universal set.

In 1230, the processing device 140 (e.g., the shape estimation module 1130) may estimate, based on the segment shape estimation model and the input data, a plurality of target location combinations of the target treatment plan and a plurality of target segment shapes of a collimator of the radiation device. Each of the plurality of target segment shapes may correspond to one of the plurality of target location combinations. In some embodiments, the plurality of target location combinations may be within a location universal set of the segment shape estimation model. The universal set may include a plurality of discrete candidate location combinations. The plurality of target segment shapes may be within a distance universal set of the segment shape estimation model. The distance universal set may include a plurality of discrete candidate leaf locations.

In some embodiments, according to the input data, the segment shape estimation model may select, as the plurality of target location combinations, some of the candidate location combinations in the location universal set and estimate, from the distance universal set, segment shapes each of which approximates the shape of the target at one of the target location combinations. In some embodiments, the segment shape estimation model may output a plurality of candidate segment shapes of which the segment shapes corresponding to the target location combinations have real shapes and the rest segment shapes are closed shapes. The output candidate segment shapes having real shapes may be designated as the target segment shapes. The candidate location combinations corresponding to the segment shapes may be designated as the target location combinations. In some embodiments, the segment shape estimation model may directly output a plurality of target locations combinations and corresponding target segment shapes.

In some embodiments, radiation information may not be used in training or in segment shape prediction. In some embodiments, the segment shape estimation model may predict the segment shapes without an estimate of the dose distribution. In some embodiments, the segment shapes may be inferred from the relationship between the geometry of segmented structures in the one or more first target images, and the segment shapes. The addition of information such as radiation information will provide further potential for the segment shape estimation model to infer dosimetric relationships without requiring a dose calculation algorithm to estimate it, or an additional element (such as a neural network) to more explicitly make such inferences.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

ADDITIONAL STATEMENT OF INVENTION

Statement of Invention 1
A system, comprising:
at least one storage device including a set of instructions; and
at least one processor configured to communicate with the at least one storage device, wherein when executing the set of instructions, the at least one processor is configured to direct the system to perform operations including:
obtaining input data relating to a target treatment plan for performing radiotherapy on a lesion using a radiation device, the input data including a first target image of the lesion;
obtaining a segment shape estimation model; and
estimating, based on the segment shape estimation model and the input data, a plurality of target location combinations of the target treatment plan and a plurality of target segment shapes of a collimator of the radiation device, one of the plurality of target location combinations indicating a location of the collimator relative to the lesion, each of the plurality of target segment shapes corresponding to one of the plurality of target location combinations.

Statement of Invention 2
The system of invention 1, wherein the target treatment plan includes a plurality of control points, each of the plurality of target location combinations or the plurality of target segment shapes corresponding to one of the plurality of control points.

Statement of Invention 3
The system of invention 1 or 2, wherein the input data includes at least one of a second target image of normal tissue surrounding the lesion, a third target image of the lesion, or target radiation information of the target treatment plan, the target radiation information including at least one of an output dose, a dose output rate, a dose per pulse, or a dose distribution in the lesion.

Statement of Invention 4
The system of invention 3, wherein the target radiation information is predicted based on the first target image of the lesion, the second target image of normal tissue surrounding the lesion, and the third target image of the lesion.

Statement of Invention 5
The system of any one of inventions 1-4, wherein one of the plurality of target location combinations includes a combination of one or more locations where one or more components of the radiation device operate.

Statement of Invention 6
The system of invention 5, wherein the one of the plurality of target location combination includes a gantry angle of a gantry of the radiation device.

Statement of Invention 7
The system of invention 5, wherein the one of the plurality of target location combination includes a combination of a gantry angle of a gantry of the radiation device and a collimator angle of the collimator of the radiation device.

Statement of Invention 8
The system of invention 5, wherein the one of the plurality of target location combination includes a combination of a gantry angle of a gantry of the radiation device, a collimator angle of the collimator of the radiation device, and a position of a couch of the radiation device.

Statement of Invention 9
The system of any one of inventions 1-8, wherein
the collimator includes a plurality of pairs of leaves; and
one of the plurality of target segment shapes of the collimator includes leaf location of each of the plurality of pairs of leaves.

Statement of Invention 10
The system of invention 9, wherein the leaf location of one of the plurality of pairs of leaves includes a location of a center of an opening of the pair of leaves and a width of the opening of the pairs of leaves.

Statement of Invention 11
The system of any one of inventions 1-10, wherein the plurality of target location combinations are within a plurality of discrete candidate location combinations of a location universal set.

Statement of Invention 12
The system of invention 11, wherein the segment shape estimation model is obtained by performing a training process including:
obtaining the location universal set including the plurality of candidate location combinations; and
determining the segment shape estimation model by iteratively training a preliminary model based on the location universal set.

Statement of Invention 13

The system of invention 12, wherein obtaining the location universal set including the plurality of candidate location combinations includes:
- obtaining a plurality of candidate gantry angles, a plurality of candidate collimator angles, or a plurality of candidate couch locations; and
- obtaining the location universal set based on the plurality of candidate gantry angles, the plurality of candidate collimator angles, or the plurality of candidate couch locations.

Statement of Invention 14

The system of invention 12 or 13, wherein the plurality of target segment shapes are within a distance universal set including a plurality of discrete candidate leaf locations.

Statement of Invention 15

The system of invention 14, wherein the training process includes:
- obtaining the distance universal set including the plurality of candidate leaf locations; and
- determining the segment shape estimation model by iteratively training the preliminary model based on the distance universal set so that the candidate segment shape corresponding to each of the plurality of candidate location combinations output by the segment shape estimation model is within the distance universal set.

Statement of Invention 16

The system of invention 15, wherein the plurality of candidate leaf locations include a plurality of candidate opening locations and a plurality of candidate opening widths.

Statement of Invention 17

The system of invention 15 or 16, wherein the training process includes:
- obtaining training data including a plurality of training sets.

Statement of Invention 18

The system of invention 17, wherein obtaining the training data includes:
- for one of the plurality of training sets,
  - obtaining a historical treatment plan previously generated based on a sample lesion;
  - obtaining a first sample image of the sample lesion corresponding to the historical treatment plan;
  - obtaining sample location combinations and corresponding sample segment shapes in the historical treatment plan; and
  - obtaining the training set based on the first sample image, the sample location combinations, and the sample segment shapes of historical treatment plan.

Statement of Invention 19

The system of invention 18, wherein obtaining the training set based on the first sample image, the sample location combinations, and the sample segment shapes of the historical treatment plan includes:
- obtaining processed sample location combinations that are within the location universal set, the processed sample location combinations being obtained by processing the sample location combinations based on the location universal set;
- obtaining processed sample segment shapes that are within the distance universal set, the processed sample segment shapes being obtained by processing the sample segment shapes based on the distance universal set;
- obtaining a sample set including the processed sample segment shapes and closed segment shapes, the closed segment shapes corresponding to the candidate location combinations excluding the processed sample location combinations; and
- obtaining the training set by including the first sample image, the processed sample location combinations, and the sample set of the historical treatment plan.

Statement of Invention 20

The system of invention 19, wherein the training process includes:
- initializing the preliminary model; and
- obtaining the segment shape estimation model by updating the initialized preliminary model using an iteration process including a plurality of iterations, at least one of the plurality of iterations of the iteration process including:
  - obtaining one of the plurality of training sets;
  - generating estimated segment shapes corresponding to the plurality of candidate location combinations by inputting the first sample image of the training set into an intermediate model, the intermediate model being the initialized preliminary model in a first iteration of the plurality of iterations of the iteration process or a previously updated model generated in a previous iteration in the iteration process;
  - determining a value of a loss function based on the estimated segment shapes and the sample set in the training set;
  - determining whether a termination condition is satisfied;
  - in response to determining that the termination condition is not satisfied,
    - generating an updated model by updating the intermediate model based on the value of the loss function; and
    - initiating a next iteration; and
  - designating the intermediate model in a last iteration of the plurality of iterations of the iteration process as the segment shape estimation model.

Statement of Invention 21

The system of invention 20, wherein the at least one of the plurality of iterations of the iteration process includes:
- in response to determining that the termination condition is satisfied, terminating the iteration process.

Statement of Invention 22

The system of invention 20 or 21, wherein the value of the loss function is determined based on sparsity of the sample set, the sparsity of the sample set relating to the closed segment shapes in the sample set.

Statement of Invention 23

The system of any one of inventions 20-22, wherein the termination condition relates to at least one of the value of the loss function or a count of iterations of the iteration process that have been performed.

Statement of Invention 24

The system of any one of inventions 20-23, wherein the training set includes at least one of a second sample image of normal tissue surrounding the sample lesion, a third sample image of the sample lesion, or sample radiation information of the historical treatment plan, the sample radiation information including at least one of a sample output dose, a sample dose output rate, a sample dose per pulse, or a sample dose distribution in the sample lesion.

Statement of Invention 25

The system of invention 24, wherein the sample radiation information is predicted based on the first sample image of the sample lesion, the second sample image of normal tissue surrounding the sample lesion, and the third sample image of the sample lesion.

Statement of Invention 26

The system of invention 24 or 25, wherein the at least one of the plurality of iterations of the iteration process includes:
generating the estimated segment shapes by inputting at least one of the second sample image, the third sample image, or the sample radiation information of the training set into the intermediate model.

Statement of Invention 27

The system of invention 24 or 25, wherein the at least one of the plurality of iterations of the iteration process includes:
determining estimated radiation information based on the estimated segment shapes;
comparing the estimated radiation information and the sample radiation information; and
generating the updated model by updating the intermediate model based on the comparison.

Statement of Invention 28

A system, comprising:
at least one storage device including a set of instructions; and
at least one processor configured to communicate with the at least one storage device, wherein when executing the set of instructions, the at least one processor is configured to direct the system to perform operations including:
obtaining a preliminary model;
obtaining training data; and
obtaining a segment shape estimation model by training the preliminary model based on the training data, the segment shape estimation model being configured to estimate, based on input data, a plurality of target location combinations in a target treatment plan for performing radiotherapy on a lesion using a radiation device and a plurality of target segment shapes of a collimator of the radiation device, the input data including a first target image of the lesion, each of the plurality of target segment shapes corresponding to one of the plurality of target location combinations, one of the plurality of target location combinations indicating a location of the collimator relative to the lesion.

Statement of Invention 29

The system of invention 28, wherein the target treatment plan includes a plurality of control points, each of the plurality of target location combinations or the plurality of target segment shapes corresponding to one of the plurality of control points.

Statement of Invention 30

The system of invention 28 or 29, wherein the input data includes at least one of a second target image of normal tissue surrounding the lesion, a third target image of the lesion, or target radiation information of the target treatment plan, the target radiation information including at least one of an output dose, a dose output rate, a dose per pulse, or a dose distribution in the lesion.

Statement of Invention 31

The system of invention 30, wherein the target radiation information is predicted based on the first target image of the lesion, the second target image of normal tissue surrounding the lesion, and the third target image of the lesion.

Statement of Invention 32

The system of any one of inventions 28-31, wherein one of the plurality of target location combinations includes a combination of one or more locations where one or more components of the radiation device operate.

Statement of Invention 33

The system of invention 32, wherein the one of the plurality of target location combination includes a gantry angle of a gantry of the radiation device.

Statement of Invention 34

The system of invention 32, wherein the one of the plurality of target location combination includes a combination of a gantry angle of a gantry of the radiation device and a collimator angle of the collimator of the radiation device.

Statement of Invention 35

The system of invention 32, wherein the one of the plurality of target location combination includes a combination of a gantry angle of a gantry of the radiation device, a collimator angle of the collimator of the radiation device, and a position of a couch of the radiation device.

Statement of Invention 36

The system of any one of inventions 28-35, wherein
the collimator includes a plurality of pairs of leaves; and
one of the plurality of target segment shapes of the collimator includes leaf location of each of the plurality of pairs of leaves.

Statement of Invention 37

The system of invention 36, wherein the leaf location of one of the plurality of pairs of leaves includes a location of a center of an opening of the pair of leaves and a width of the opening of the pairs of leaves.

Statement of Invention 38

The system of any one of inventions 28-37, wherein the plurality of target location combinations are within a location universal set including a plurality of discrete candidate location combinations.

Statement of Invention 39

The system of invention 38, wherein obtaining the preliminary model includes:
obtaining the location universal set including the plurality of candidate location combinations; and
obtaining the preliminary model based on the location universal set.

Statement of Invention 40

The system of invention 39, wherein obtaining the location universal set including the plurality of candidate location combinations includes:
obtaining a plurality of candidate gantry angles, a plurality of candidate collimator angles, or a plurality of candidate couch locations; and
obtaining the location universal set based on the plurality of candidate gantry angles, the plurality of candidate collimator angles, or the plurality of candidate couch locations.

Statement of Invention 41

The system of invention 39 or 40, wherein the plurality of target segment shapes are within a distance universal set including a plurality of discrete candidate leaf locations.

Statement of Invention 42

The system of invention 41, wherein obtaining the preliminary model includes:
obtaining the distance universal set including the plurality of candidate leaf locations; and
obtaining the preliminary model includes based on the distance universal set so that the candidate segment shape corresponding to each of the plurality of candidate location combinations output by the segment shape estimation model is within the distance universal set.

Statement of Invention 43

The system of invention 42, wherein the plurality of candidate leaf locations include a plurality of candidate opening locations and a plurality of candidate opening widths.

Statement of Invention 44

The system of invention 42 or 43, wherein obtaining the training data includes:
for one of a plurality of training sets of the training data,
obtaining a historical treatment plan previously generated based on a sample lesion;
obtaining a first sample image of the sample lesion corresponding to the historical treatment plan;
obtaining sample location combinations and corresponding sample segment shapes in the historical treatment plan; and
obtaining the training set based on the first sample image, the sample location combinations, and the sample segment shapes of historical treatment Statement of Invention 45

The system of invention 44, wherein obtaining the training set based on the first sample image, the sample location combinations, and the sample segment shapes of the historical treatment plan includes:
obtaining processed sample location combinations that are within the location universal set, the processed sample location combinations being obtained by processing the sample location combinations based on the location universal set;
obtaining processed sample segment shapes that are within the distance universal set, the processed sample segment shapes being obtained by processing the sample segment shapes based on the distance universal set;
obtaining a sample set including the processed sample segment shapes and closed segment shapes, the closed segment shapes corresponding to the candidate location combinations excluding the processed sample location combinations; and
obtaining the training set by including the first sample image, the processed sample location combinations, and the sample set of the historical treatment plan.

Statement of Invention 46

The system of invention 45, wherein obtaining the segment shape estimation model by training the preliminary model based on the training data includes:
initializing the preliminary model; and
obtaining the segment shape estimation model by updating the initialized preliminary model using an iteration process including a plurality of iterations, at least one of the plurality of iterations of the iteration process including:
obtaining one of the plurality of training sets;
generating estimated segment shapes corresponding to the plurality of candidate location combinations by inputting the first sample image of the training set into an intermediate model, the intermediate model being the initialized preliminary model in a first iteration of the plurality of iterations of the iteration process or a previously updated model generated in a previous iteration in the iteration process;
determining a value of a loss function based on the estimated segment shapes and the sample set in the training set;
determining whether a termination condition is satisfied;
in response to determining that the termination condition is not satisfied,
generating an updated model by updating the intermediate model based on the value of the loss function; and
initiating a next iteration; and
designating the intermediate model in a last iteration of the plurality of iterations of the iteration process as the segment shape estimation model.

Statement of Invention 47

The system of invention 46, wherein the at least one of the plurality of iterations of the iteration process includes:
in response to determining that the termination condition is satisfied, terminating the iteration process.

Statement of Invention 48

The system of invention 46 or 47, wherein the value of the loss function is determined based on sparsity of the sample set, the sparsity of the sample set relating to the closed segment shapes in the sample set.

Statement of Invention 49

The system of any one of inventions 46-48, wherein the termination condition relates to at least one of the value of the loss function or a count of iterations of the iteration process that have been performed.

Statement of Invention 50

The system of any one of inventions 46-49, wherein the training set includes at least one of a second sample image of normal tissue surrounding the sample lesion, a third sample image of the sample lesion, or sample radiation information of the historical treatment plan, the sample radiation information including at least one of a sample output dose, a sample dose output rate, a sample dose per pulse, or a sample dose distribution in the sample lesion.

Statement of Invention 51

The system of invention 50, wherein the sample radiation information is predicted based on the first sample image of the sample lesion, the second sample image of normal tissue surrounding the sample lesion, and the third sample image of the sample lesion.

Statement of Invention 52

The system of invention 50 or 51, wherein the at least one of the plurality of iterations of the iteration process includes:
generating the estimated segment shapes by inputting at least one of the processed location combinations, the second sample image, the third sample image, or the sample radiation information of the training set into the intermediate model.

Statement of Invention 53

The system of invention 52, wherein the at least one of the plurality of iterations of the iteration process includes:
determining estimated radiation information based on the estimated segment shapes;
comparing the estimated radiation information and the sample radiation information; and
generating the updated model by updating the intermediate model based on the comparison.

Statement of Invention 54

A method implemented on a machine including one or more processors and one or more storage devices, comprising:
obtaining input data relating to a target treatment plan for performing radiotherapy on a lesion using a radiation device, the input data including a first target image of the lesion;
obtaining a segment shape estimation model; and
estimating, based on the segment shape estimation model and the input data, a plurality of target location combinations of the target treatment plan and a plurality of target segment shapes of a collimator of the radiation device, one of the plurality of target location combinations indicating a location of the collimator relative to the lesion, each of the plurality of target segment shapes corresponding to one of the plurality of target location combinations.

Statement of Invention 55

The method of invention 54, wherein the target treatment plan includes a plurality of control points, each of the plurality of target location combinations or the plurality of target segment shapes corresponding to one of the plurality of control points.

Statement of Invention 56

The method of invention 55 or 56, wherein the input data includes at least one of a second target image of normal tissue surrounding the lesion, a third target image of the lesion, or target radiation information of the target treatment plan, the target radiation information including at least one of an output dose, a dose output rate, a dose per pulse, or a dose distribution in the lesion.

Statement of Invention 57

The method of invention 56, wherein the target radiation information is predicted based on the first target image of the lesion, the second target image of normal tissue surrounding the lesion, and the third target image of the lesion.

Statement of Invention 58

The method of any one of inventions 54-57, wherein one of the plurality of target location combinations includes a combination of one or more locations where one or more components of the radiation device operate.

Statement of Invention 59

The method of invention 58, wherein the one of the plurality of target location combination includes a gantry angle of a gantry of the radiation device.

Statement of Invention 60

The method of invention 58, wherein the one of the plurality of target location combination includes a combination of a gantry angle of a gantry of the radiation device and a collimator angle of the collimator of the radiation device.

Statement of Invention 61

The method of invention 58, wherein the one of the plurality of target location combination includes a combination of a gantry angle of a gantry of the radiation device, a collimator angle of the collimator of the radiation device, and a position of a couch of the radiation device.

Statement of Invention 62

The method of any one of inventions 54-61, wherein
the collimator includes a plurality of pairs of leaves; and
one of the plurality of target segment shapes of the collimator includes leaf location of each of the plurality of pairs of leaves.

Statement of Invention 63

The method of invention 62, wherein the leaf location of one of the plurality of pairs of leaves includes a location of a center of an opening of the pair of leaves and a width of the opening of the pairs of leaves.

Statement of Invention 64

The method of any one of inventions 54-63, wherein the plurality of target location combinations are within a plurality of discrete candidate location combinations of a location universal set.

Statement of Invention 65

The method of invention 64, wherein the segment shape estimation model is obtained by performing a training process including:

obtaining the location universal set including the plurality of candidate location combinations; and
determining the segment shape estimation model by iteratively training a preliminary model based on the location universal set.

Statement of Invention 66

The method of invention 65, wherein obtaining the location universal set including the plurality of candidate location combinations includes:

obtaining a plurality of candidate gantry angles, a plurality of candidate collimator angles, or a plurality of candidate couch locations; and
obtaining the location universal set based on the plurality of candidate gantry angles, the plurality of candidate collimator angles, or the plurality of candidate couch locations.

Statement of Invention 67

The method of invention 65 or 66, wherein the plurality of target segment shapes are within a distance universal set including a plurality of discrete candidate leaf locations.

Statement of Invention 68

The method of invention 67, wherein the training process includes:

obtaining the distance universal set including the plurality of candidate leaf locations; and
determining the segment shape estimation model by iteratively training the preliminary model based on the distance universal set so that the candidate segment shape corresponding to each of the plurality of candidate location combinations output by the segment shape estimation model is within the distance universal set.

Statement of Invention 69

The method of invention 68, wherein the plurality of candidate leaf locations include a plurality of candidate opening locations and a plurality of candidate opening widths.

Statement of Invention 70

The method of invention 68 or 69, wherein the training process includes:

obtaining training data including a plurality of training sets.

Statement of Invention 71

The method of invention 70, wherein obtaining the training data includes:

for one of the plurality of training sets,
obtaining a historical treatment plan previously generated based on a sample lesion;
obtaining a first sample image of the sample lesion corresponding to the historical treatment plan;
obtaining sample location combinations and corresponding sample segment shapes in the historical treatment plan; and
obtaining the training set based on the first sample image, the sample location combinations, and the sample segment shapes of historical treatment Statement of Invention 72

The method of invention 71, wherein obtaining the training set based on the first sample image, the sample location combinations, and the sample segment shapes of the historical treatment plan includes:

obtaining processed sample location combinations that are within the location universal set, the processed sample location combinations being obtained by processing the sample location combinations based on the location universal set;

obtaining processed sample segment shapes that are within the distance universal set, the processed sample segment shapes being obtained by processing the sample segment shapes based on the distance universal set;

obtaining a sample set including the processed sample segment shapes and closed segment shapes, the closed segment shapes corresponding to the candidate location combinations excluding the processed sample location combinations; and obtaining the training set by including the first sample image, the processed sample location combinations, and the sample set of the historical treatment plan.

Statement of Invention 73

The method of invention 72, wherein the training process includes:

initializing the preliminary model; and obtaining the segment shape estimation model by updating the initialized preliminary model using an iteration process including a plurality of iterations, at least one of the plurality of iterations of the iteration process including:

obtaining one of the plurality of training sets;

generating estimated segment shapes corresponding to the plurality of candidate location combinations by inputting the first sample image of the training set into an intermediate model, the intermediate model being the initialized preliminary model in a first iteration of the plurality of iterations of the iteration process or a previously updated model generated in a previous iteration in the iteration process;

determining a value of a loss function based on the estimated segment shapes and the sample set in the training set;

determining whether a termination condition is satisfied;

in response to determining that the termination condition is not satisfied, generating an updated model by updating the intermediate model based on the value of the loss function; and initiating a next iteration; and designating the intermediate model in a last iteration of the plurality of iterations of the iteration process as the segment shape estimation model.

Statement of Invention 74

The method of invention 73, wherein the at least one of the plurality of iterations of the iteration process includes:

in response to determining that the termination condition is satisfied, terminating the iteration process.

Statement of Invention 75

The method of invention 73 or 74, wherein the value of the loss function is determined based on sparsity of the sample set, the sparsity of the sample set relating to the closed segment shapes in the sample set.

Statement of Invention 76

The method of any one of inventions 73-75, wherein the termination condition relates to at least one of the value of the loss function or a count of iterations of the iteration process that have been performed.

Statement of Invention 77

The method of any one of inventions 73-76, wherein the training set includes at least one of a second sample image of normal tissue surrounding the sample lesion, a third sample image of the sample lesion, or sample radiation information of the historical treatment plan, the sample radiation information including at least one of a sample output dose, a sample dose output rate, a sample dose per pulse, or a sample dose distribution in the sample lesion.

Statement of Invention 78

The method of invention 77, wherein the sample radiation information is predicted based on the first sample image of the sample lesion, the second sample image of normal tissue surrounding the sample lesion, and the third sample image of the sample lesion.

Statement of Invention 79

The method of invention 77 or 78, wherein the at least one of the plurality of iterations of the iteration process includes:

generating the estimated segment shapes by inputting at least one of the second sample image, the third sample image, or the sample radiation information of the training set into the intermediate model.

Statement of Invention 80

The method of invention 77 or 78, wherein the at least one of the plurality of iterations of the iteration process includes:

determining estimated radiation information based on the estimated segment shapes;

comparing the estimated radiation information and the sample radiation information; and generating the updated model by updating the intermediate model based on the comparison.

Statement of Invention 81

A method implemented on a machine including one or more processors and one or more storage devices, comprising:

obtaining a preliminary model;

obtaining training data; and obtaining a segment shape estimation model by training the preliminary model based on the training data, the segment shape estimation model being configured to estimate, based on input data, a plurality of target location combinations in a target treatment plan for performing radiotherapy on a lesion using a radiation device and a plurality of target segment shapes of a collimator of the radiation device, the input data including a first target image of the lesion, each of the plurality of target segment shapes corresponding to one of the plurality of target location combinations, one of the plurality of target location combinations indicating a location of the collimator relative to the lesion.

Statement of Invention 82

The method of invention 81, wherein the target treatment plan includes a plurality of control points, each of the plurality of target location combinations or the plurality of target segment shapes corresponding to one of the plurality of control points.

Statement of Invention 83

The method of invention 81 or 82, wherein the input data includes at least one of a second target image of normal tissue surrounding the lesion, a third target image of the lesion, or target radiation information of the target treatment plan, the target radiation information including at least one of an output dose, a dose output rate, a dose per pulse, or a dose distribution in the lesion.

Statement of Invention 84

The method of invention 83, wherein the target radiation information is predicted based on the first target image of the lesion, the second target image of normal tissue surrounding the lesion, and the third target image of the lesion.

Statement of Invention 85

The method of any one of inventions 81-84, wherein one of the plurality of target location combinations includes a combination of one or more locations where one or more components of the radiation device operate.

Statement of Invention 86

The method of invention 85, wherein the one of the plurality of target location combination includes a gantry angle of a gantry of the radiation device.

Statement of Invention 87

The method of invention 85, wherein the one of the plurality of target location combination includes a combination of a gantry angle of a gantry of the radiation device and a collimator angle of the collimator of the radiation device.

Statement of Invention 88

The method of invention 85, wherein the one of the plurality of target location combination includes a combination of a gantry angle of a gantry of the radiation device, a collimator angle of the collimator of the radiation device, and a position of a couch of the radiation device.

Statement of Invention 89

The method of any one of inventions 81-88, wherein
the collimator includes a plurality of pairs of leaves; and
one of the plurality of target segment shapes of the collimator includes leaf location of each of the plurality of pairs of leaves.

Statement of Invention 90

The method of invention 89, wherein the leaf location of one of the plurality of pairs of leaves includes a location of a center of an opening of the pair of leaves and a width of the opening of the pairs of leaves.

Statement of Invention 91

The method of any one of inventions 81-90, wherein the plurality of target location combinations are within a location universal set including a plurality of discrete candidate location combinations.

Statement of Invention 92

The method of invention 91, wherein obtaining the preliminary model includes:
obtaining the location universal set including the plurality of candidate location combinations; and
obtaining the preliminary model based on the location universal set.

Statement of Invention 93

The method of invention 92, wherein obtaining the location universal set including the plurality of candidate location combinations includes:
obtaining a plurality of candidate gantry angles, a plurality of candidate collimator angles, or a plurality of candidate couch locations; and
obtaining the location universal set based on the plurality of candidate gantry angles, the plurality of candidate collimator angles, or the plurality of candidate couch locations.

Statement of Invention 94

The method of invention 92 or 93, wherein the plurality of target segment shapes are within a distance universal set including a plurality of discrete candidate leaf locations.

Statement of Invention 95

The method of invention 94, wherein obtaining the preliminary model includes:
obtaining the distance universal set including the plurality of candidate leaf locations; and
obtaining the preliminary model includes based on the distance universal set so that the candidate segment shape corresponding to each of the plurality of candidate location combinations output by the segment shape estimation model is within the distance universal set.

Statement of Invention 96

The method of invention 95, wherein the plurality of candidate leaf locations include a plurality of candidate opening locations and a plurality of candidate opening widths.

Statement of Invention 97

The method of invention 95 or 96, wherein obtaining the training data includes:
for one of a plurality of training sets of the training data,
obtaining a historical treatment plan previously generated based on a sample lesion;
obtaining a first sample image of the sample lesion corresponding to the historical treatment plan;
obtaining sample location combinations and corresponding sample segment shapes in the historical treatment plan; and
obtaining the training set based on the first sample image, the sample location combinations, and the sample segment shapes of historical treatment plan.

Statement of Invention 98

The method of invention 97, wherein obtaining the training set based on the first sample image, the sample location combinations, and the sample segment shapes of the historical treatment plan includes:
obtaining processed sample location combinations that are within the location universal set, the processed sample location combinations being obtained by processing the sample location combinations based on the location universal set;
obtaining processed sample segment shapes that are within the distance universal set, the processed sample segment shapes being obtained by processing the sample segment shapes based on the distance universal set;
obtaining a sample set including the processed sample segment shapes and closed segment shapes, the closed segment shapes corresponding to the candidate location combinations excluding the processed sample location combinations; and obtaining the training set by including the first sample image, the processed sample location combinations, and the sample set of the historical treatment plan.

Statement of Invention 99

The method of invention 98, wherein obtaining the segment shape estimation model by training the preliminary model based on the training data includes:
initializing the preliminary model; and
obtaining the segment shape estimation model by updating the initialized preliminary model using an iteration process including a plurality of iterations, at least one of the plurality of iterations of the iteration process including:
obtaining one of the plurality of training sets;
generating estimated segment shapes corresponding to the plurality of candidate location combinations by inputting the first sample image of the training set into an intermediate model, the intermediate model being the initialized preliminary model in a first iteration of the plurality of iterations of the iteration process or a previously updated model generated in a previous iteration in the iteration process;
determining a value of a loss function based on the estimated segment shapes and the sample set in the training set;
determining whether a termination condition is satisfied;
in response to determining that the termination condition is not satisfied, generating an updated model by updating the intermediate model based on the value of the loss function; and
initiating a next iteration; and
designating the intermediate model in a last iteration of the plurality of iterations of the iteration process as the segment shape estimation model.

Statement of Invention 100
The method of invention 99, wherein the at least one of the plurality of iterations of the iteration process includes:
in response to determining that the termination condition is satisfied, terminating the iteration process.

Statement of Invention 101
The method of invention 99 or 100, wherein the value of the loss function is determined based on sparsity of the sample set, the sparsity of the sample set relating to the closed segment shapes in the sample set.

Statement of Invention 102
The method of any one of inventions 99-101, wherein the termination condition relates to at least one of the value of the loss function or a count of iterations of the iteration process that have been performed.

Statement of Invention 103
The method of any one of inventions 99-102, wherein the training set includes at least one of a second sample image of normal tissue surrounding the sample lesion, a third sample image of the sample lesion, or sample radiation information of the historical treatment plan, the sample radiation information including at least one of a sample output dose, a sample dose output rate, a sample dose per pulse, or a sample dose distribution in the sample lesion.

Statement of Invention 104
The method of invention 103, wherein the sample radiation information is predicted based on the first sample image of the sample lesion, the second sample image of normal tissue surrounding the sample lesion, and the third sample image of the sample lesion.

Statement of Invention 105
The method of invention 103 or 104, wherein the at least one of the plurality of iterations of the iteration process includes:
generating the estimated segment shapes by inputting at least one of the processed location combinations, the second sample image, the third sample image, or the sample radiation information of the training set into the intermediate model.

Statement of Invention 106
The method of invention 105, wherein the at least one of the plurality of iterations of the iteration process includes:
determining estimated radiation information based on the estimated segment shapes;
comparing the estimated radiation information and the sample radiation information; and
generating the updated model by updating the intermediate model based on the comparison.

Statement of Invention 107
A system, comprising:
an input obtaining module configured to obtain input data relating to a target treatment plan for performing radiotherapy on a lesion using a radiation device, the input data including a first target image of the lesion;
a model obtaining module configured to obtain a segment shape estimation model; and
a shape estimation module configured to estimate, based on the segment shape estimation model and the input data, a plurality of target location combinations of the target treatment plan and a plurality of target segment shapes of a collimator of the radiation device, one of the plurality of target location combinations indicating a location of the collimator relative to the lesion, each of the plurality of target segment shapes corresponding to one of the plurality of target location combinations.

Statement of Invention 108
The system of invention 107, wherein the target treatment plan includes a plurality of control points, each of the plurality of target location combinations or the plurality of target segment shapes corresponding to one of the plurality of control points.

Statement of Invention 109
The system of invention 107 or 108, wherein the input data includes at least one of a second target image of normal tissue surrounding the lesion, a third target image of the lesion, or target radiation information of the target treatment plan, the target radiation information including at least one of an output dose, a dose output rate, a dose per pulse, or a dose distribution in the lesion.

Statement of Invention 110
The system of invention 109, wherein the target radiation information is predicted based on the first target image of the lesion, the second target image of normal tissue surrounding the lesion, and the third target image of the lesion.

Statement of Invention 111
The system of any one of inventions 107-110, wherein one of the plurality of target location combinations includes a combination of one or more locations where one or more components of the radiation device operate.

Statement of Invention 112
The system of invention 111, wherein the one of the plurality of target location combination includes a gantry angle of a gantry of the radiation device.

Statement of Invention 113
The system of invention 111, wherein the one of the plurality of target location combination includes a combination of a gantry angle of a gantry of the radiation device and a collimator angle of the collimator of the radiation device.

Statement of Invention 114
The system of invention 111, wherein the one of the plurality of target location combination includes a combination of a gantry angle of a gantry of the radiation device, a collimator angle of the collimator of the radiation device, and a position of a couch of the radiation device.

Statement of Invention 115
The system of any one of inventions 107-114, wherein the collimator includes a plurality of pairs of leaves; and
one of the plurality of target segment shapes of the collimator includes leaf location of each of the plurality of pairs of leaves.

Statement of Invention 116
The system of invention 115, wherein the leaf location of one of the plurality of pairs of leaves includes a location of a center of an opening of the pair of leaves and a width of the opening of the pairs of leaves.

Statement of Invention 117
The system of any one of inventions 107-116, wherein the plurality of target location combinations are within a plurality of discrete candidate location combinations of a location universal set.

Statement of Invention 118
The system of invention 117, wherein the segment shape estimation model is obtained by performing a training process including:
obtaining the location universal set including the plurality of candidate location combinations; and determining the segment shape estimation model by iteratively training a preliminary model based on the location universal set.

Statement of Invention 119

The system of invention 118, wherein obtaining the location universal set including the plurality of candidate location combinations includes:
obtaining a plurality of candidate gantry angles, a plurality of candidate collimator angles, or a plurality of candidate couch locations; and
obtaining the location universal set based on the plurality of candidate gantry angles, the plurality of candidate collimator angles, or the plurality of candidate couch locations.

Statement of Invention 120

The system of invention 118 or 119, wherein the plurality of target segment shapes are within a distance universal set including a plurality of discrete candidate leaf locations.

Statement of Invention 121

The system of invention 120, wherein the training process includes:
obtaining the distance universal set including the plurality of candidate leaf locations; and
determining the segment shape estimation model by iteratively training the preliminary model based on the distance universal set so that the candidate segment shape corresponding to each of the plurality of candidate location combinations output by the segment shape estimation model is within the distance universal set.

Statement of Invention 122

The system of invention 121, wherein the plurality of candidate leaf locations include a plurality of candidate opening locations and a plurality of candidate opening widths.

Statement of Invention 123

The system of invention 121 or 122, wherein the training process includes:
obtaining training data including a plurality of training sets.

Statement of Invention 124

The system of invention 123, wherein obtaining the training data includes:
for one of the plurality of training sets,
  obtaining a historical treatment plan previously generated based on a sample lesion;
  obtaining a first sample image of the sample lesion corresponding to the historical treatment plan;
  obtaining sample location combinations and corresponding sample segment shapes in the historical treatment plan; and
  obtaining the training set based on the first sample image, the sample location combinations, and the sample segment shapes of historical treatment plan.

Statement of Invention 125

The system of invention 124, wherein obtaining the training set based on the first sample image, the sample location combinations, and the sample segment shapes of the historical treatment plan includes:
obtaining processed sample location combinations that are within the location universal set, the processed sample location combinations being obtained by processing the sample location combinations based on the location universal set;
obtaining processed sample segment shapes that are within the distance universal set, the processed sample segment shapes being obtained by processing the sample segment shapes based on the distance universal set;
obtaining a sample set including the processed sample segment shapes and closed segment shapes, the closed segment shapes corresponding to the candidate location combinations excluding the processed sample location combinations; and
obtaining the training set by including the first sample image, the processed sample location combinations, and the sample set of the historical treatment plan.

Statement of Invention 126

The system of invention 125, wherein the training process includes:
initializing the preliminary model; and
obtaining the segment shape estimation model by updating the initialized preliminary model using an iteration process including a plurality of iterations, at least one of the plurality of iterations of the iteration process including:
  obtaining one of the plurality of training sets;
  generating estimated segment shapes corresponding to the plurality of candidate location combinations by inputting the first sample image of the training set into an intermediate model, the intermediate model being the initialized preliminary model in a first iteration of the plurality of iterations of the iteration process or a previously updated model generated in a previous iteration in the iteration process;
  determining a value of a loss function based on the estimated segment shapes and the sample set in the training set;
  determining whether a termination condition is satisfied;
  in response to determining that the termination condition is not satisfied,
    generating an updated model by updating the intermediate model based on the value of the loss function; and
    initiating a next iteration; and
  designating the intermediate model in a last iteration of the plurality of iterations of the iteration process as the segment shape estimation model.

Statement of Invention 127

The system of invention 126, wherein the at least one of the plurality of iterations of the iteration process includes:
in response to determining that the termination condition is satisfied, terminating the iteration process.

Statement of Invention 128

The system of invention 126 or 127, wherein the value of the loss function is determined based on sparsity of the sample set, the sparsity of the sample set relating to the closed segment shapes in the sample set.

Statement of Invention 129

The system of any one of inventions 126-128, wherein the termination condition relates to at least one of the value of the loss function or a count of iterations of the iteration process that have been performed.

Statement of Invention 130

The system of any one of inventions 126-129, wherein the training set includes at least one of a second sample image of normal tissue surrounding the sample lesion, a third sample image of the sample lesion, or sample radiation information of the historical treatment plan, the sample radiation information including at least one of a sample output dose, a sample dose output rate, a sample dose per pulse, or a sample dose distribution in the sample lesion.

Statement of Invention 131
The system of invention 130, wherein the sample radiation information is predicted based on the first sample image of the sample lesion, the second sample image of normal tissue surrounding the sample lesion, and the third sample image of the sample lesion.
Statement of Invention 132
The system of invention 130 or 131, wherein the at least one of the plurality of iterations of the iteration process includes:
generating the estimated segment shapes by inputting at least one of the second sample image, the third sample image, or the sample radiation information of the training set into the intermediate model.
Statement of Invention 133
The system of invention 130 or 131, wherein the at least one of the plurality of iterations of the iteration process includes:
determining estimated radiation information based on the estimated segment shapes;
comparing the estimated radiation information and the sample radiation information; and
generating the updated model by updating the intermediate model based on the comparison.
Statement of Invention 134
A system, comprising a model obtaining module configured to:
obtain a preliminary model;
obtain training data; and
obtain a segment shape estimation model by training the preliminary model based on the training data, the segment shape estimation model being configured to estimate, based on input data, a plurality of target location combinations in a target treatment plan for performing radiotherapy on a lesion using a radiation device and a plurality of target segment shapes of a collimator of the radiation device, the input data including a first target image of the lesion, each of the plurality of target segment shapes corresponding to one of the plurality of target location combinations, one of the plurality of target location combinations indicating a location of the collimator relative to the lesion.
Statement of Invention 135
The system of invention 134, wherein the target treatment plan includes a plurality of control points, each of the plurality of target location combinations or the plurality of target segment shapes corresponding to one of the plurality of control points.
Statement of Invention 136
The system of invention 134 or 135, wherein the input data includes at least one of a second target image of normal tissue surrounding the lesion, a third target image of the lesion, or target radiation information of the target treatment plan, the target radiation information including at least one of an output dose, a dose output rate, a dose per pulse, or a dose distribution in the lesion.
Statement of Invention 137
The system of invention 136, wherein the target radiation information is predicted based on the first target image of the lesion, the second target image of normal tissue surrounding the lesion, and the third target image of the lesion.
Statement of Invention 138
The system of any one of inventions 134-137, wherein one of the plurality of target location combinations includes a combination of one or more locations where one or more components of the radiation device operate.
Statement of Invention 139
The system of invention 138, wherein the one of the plurality of target location combination includes a gantry angle of a gantry of the radiation device.
Statement of Invention 140
The system of invention 138, wherein the one of the plurality of target location combination includes a combination of a gantry angle of a gantry of the radiation device and a collimator angle of the collimator of the radiation device.
Statement of Invention 141
The system of invention 138, wherein the one of the plurality of target location combination includes a combination of a gantry angle of a gantry of the radiation device, a collimator angle of the collimator of the radiation device, and a position of a couch of the radiation device.
Statement of Invention 142
The system of any one of inventions 134-141, wherein
the collimator includes a plurality of pairs of leaves; and
one of the plurality of target segment shapes of the collimator includes leaf location of each of the plurality of pairs of leaves.
Statement of Invention 143
The system of invention 142, wherein the leaf location of one of the plurality of pairs of leaves includes a location of a center of an opening of the pair of leaves and a width of the opening of the pairs of leaves.
Statement of Invention 144
The system of any one of inventions 141-143, wherein the plurality of target location combinations are within a location universal set including a plurality of discrete candidate location combinations.
Statement of Invention 145
The system of invention 144, wherein obtaining the preliminary model includes:
obtaining the location universal set including the plurality of candidate location combinations; and
obtaining the preliminary model based on the location universal set.
Statement of Invention 146
The system of invention 145, wherein obtaining the location universal set including the plurality of candidate location combinations includes:
obtaining a plurality of candidate gantry angles, a plurality of candidate collimator angles, or a plurality of candidate couch locations; and
obtaining the location universal set based on the plurality of candidate gantry angles, the plurality of candidate collimator angles, or the plurality of candidate couch locations.
Statement of Invention 147
The system of invention 145 or 146, wherein the plurality of target segment shapes are within a distance universal set including a plurality of discrete candidate leaf locations.
Statement of Invention 148
The system of invention 147, wherein obtaining the preliminary model includes:
obtaining the distance universal set including the plurality of candidate leaf locations; and
obtaining the preliminary model includes based on the distance universal set so that the candidate segment shape corresponding to each of the plurality of candidate location combinations output by the segment shape estimation model is within the distance universal set.

Statement of Invention 149

The system of invention 148, wherein the plurality of candidate leaf locations include a plurality of candidate opening locations and a plurality of candidate opening widths.

Statement of Invention 150

The system of invention 148 or 149, wherein obtaining the training data includes:
- for one of a plurality of training sets of the training data,
  - obtaining a historical treatment plan previously generated based on a sample lesion;
  - obtaining a first sample image of the sample lesion corresponding to the historical treatment plan;
  - obtaining sample location combinations and corresponding sample segment shapes in the historical treatment plan; and
  - obtaining the training set based on the first sample image, the sample location combinations, and the sample segment shapes of historical treatment plan.

Statement of Invention 151

The system of invention 150, wherein obtaining the training set based on the first sample image, the sample location combinations, and the sample segment shapes of the historical treatment plan includes:
- obtaining processed sample location combinations that are within the location universal set, the processed sample location combinations being obtained by processing the sample location combinations based on the location universal set;
- obtaining processed sample segment shapes that are within the distance universal set, the processed sample segment shapes being obtained by processing the sample segment shapes based on the distance universal set;
- obtaining a sample set including the processed sample segment shapes and closed segment shapes, the closed segment shapes corresponding to the candidate location combinations excluding the processed sample location combinations; and
- obtaining the training set by including the first sample image, the processed sample location combinations, and the sample set of the historical treatment plan.

Statement of invention 152

The system of invention 151, wherein obtaining the segment shape estimation model by training the preliminary model based on the training data includes:
- initializing the preliminary model; and
- obtaining the segment shape estimation model by updating the initialized preliminary model using an iteration process including a plurality of iterations, at least one of the plurality of iterations of the iteration process including:
  - obtaining one of the plurality of training sets;
  - generating estimated segment shapes corresponding to the plurality of candidate location combinations by inputting the first sample image of the training set into an intermediate model, the intermediate model being the initialized preliminary model in a first iteration of the plurality of iterations of the iteration process or a previously updated model generated in a previous iteration in the iteration process;
  - determining a value of a loss function based on the estimated segment shapes and the sample set in the training set;
  - determining whether a termination condition is satisfied;
  - in response to determining that the termination condition is not satisfied,
    - generating an updated model by updating the intermediate model based on the value of the loss function; and
    - initiating a next iteration; and
  - designating the intermediate model in a last iteration of the plurality of iterations of the iteration process as the segment shape estimation model.

Statement of Invention 153

The system of invention 152, wherein the at least one of the plurality of iterations of the iteration process includes:
- in response to determining that the termination condition is satisfied, terminating the iteration process.

Statement of Invention 154

The system of invention 152 or 153, wherein the value of the loss function is determined based on sparsity of the sample set, the sparsity of the sample set relating to the closed segment shapes in the sample set.

Statement of Invention 155

The system of any one of inventions 152-154, wherein the termination condition relates to at least one of the value of the loss function or a count of iterations of the iteration process that have been performed.

Statement of Invention 156

The system of any one of inventions 152-155, wherein the training set includes at least one of a second sample image of normal tissue surrounding the sample lesion, a third sample image of the sample lesion, or sample radiation information of the historical treatment plan, the sample radiation information including at least one of a sample output dose, a sample dose output rate, a sample dose per pulse, or a sample dose distribution in the sample lesion.

Statement of Invention 157

The system of invention 156, wherein the sample radiation information is predicted based on the first sample image of the sample lesion, the second sample image of normal tissue surrounding the sample lesion, and the third sample image of the sample lesion.

Statement of Invention 158

The system of invention 156 or 157, wherein the at least one of the plurality of iterations of the iteration process includes:
- generating the estimated segment shapes by inputting at least one of the processed location combinations, the second sample image, the third sample image, or the sample radiation information of the training set into the intermediate model.

Statement of Invention 159

The system of invention 158, wherein the at least one of the plurality of iterations of the iteration process includes:
- determining estimated radiation information based on the estimated segment shapes;
- comparing the estimated radiation information and the sample radiation information; and
- generating the updated model by updating the intermediate model based on the comparison.

Statement of Invention 160

A non-transitory computer readable medium, comprising at least one set of instructions, wherein when executed by one or more processors of a computing device, the at least one set of instructions causes the computing device to perform a method, the method comprising:
- obtaining input data relating to a target treatment plan for performing radiotherapy on a lesion using a radiation device, the input data including a first target image of the lesion;

obtaining a segment shape estimation model; and estimating, based on the segment shape estimation model and the input data, a plurality of target location combinations of the target treatment plan and a plurality of target segment shapes of a collimator of the radiation device, one of the plurality of target location combinations indicating a location of the collimator relative to the lesion, each of the plurality of target segment shapes corresponding to one of the plurality of target location combinations.

Statement of Invention 161

A non-transitory computer readable medium, comprising at least one set of instructions for identifying a road feature, wherein when executed by one or more processors of a computing device, the at least one set of instructions causes the computing device to perform a method, the method comprising:

obtaining a preliminary model;

obtaining training data; and obtaining a segment shape estimation model by training the preliminary model based on the training data, the segment shape estimation model being configured to estimate, based on input data, a plurality of target location combinations in a target treatment plan for performing radiotherapy on a lesion using a radiation device and a plurality of target segment shapes of a collimator of the radiation device, the input data including a first target image of the lesion, each of the plurality of target segment shapes corresponding to one of the plurality of target location combinations, one of the plurality of target location combinations indicating a location of the collimator relative to the lesion.

What is claimed is:

1. A system, comprising:

at least one storage device including a set of instructions; and at least one processor configured to communicate with the at least one storage device, wherein when executing the set of instructions, the at least one processor is configured to direct the system to perform operations including:

obtaining input data relating to a target treatment plan for performing radiotherapy on a lesion using a radiation device, the input data including a first target image of the lesion;

obtaining a segment shape estimation model; and estimating, based on the segment shape estimation model and the input data, a plurality of target location combinations of the target treatment plan and a plurality of target segment shapes of a collimator of the radiation device, one of the plurality of target location combinations indicating a location of the collimator relative to the lesion, each of the plurality of target segment shapes corresponding to one of the plurality of target location combinations.

2. The system of claim 1, wherein the plurality of target location combinations are within a plurality of discrete candidate location combinations of a location universal set.

3. The system of claim 2, wherein the segment shape estimation model is obtained by performing a training process including:

obtaining the location universal set including the plurality of candidate location combinations; and determining the segment shape estimation model by iteratively training a preliminary model based on the location universal set.

4. The system of claim 3, wherein obtaining the location universal set including the plurality of candidate location combinations includes:

obtaining a plurality of candidate gantry angles, a plurality of candidate collimator angles, or a plurality of candidate couch locations; and obtaining the location universal set based on the plurality of candidate gantry angles, the plurality of candidate collimator angles, or the plurality of candidate couch locations.

5. The system of claim 3, wherein the plurality of target segment shapes are within a distance universal set including a plurality of discrete candidate leaf locations.

6. The system of claim 5, wherein the training process includes:

obtaining the distance universal set including the plurality of candidate leaf locations; and determining the segment shape estimation model by iteratively training the preliminary model based on the distance universal set so that the candidate segment shape corresponding to each of the plurality of candidate location combinations output by the segment shape estimation model is within the distance universal set.

7. The system of claim 6, wherein the plurality of candidate leaf locations include a plurality of candidate opening locations and a plurality of candidate opening widths.

8. The system of claim 6, wherein the training process includes:

obtaining training data including a plurality of training sets.

9. The system of claim 8, wherein obtaining the training data includes:

for one of the plurality of training sets, obtaining a historical treatment plan previously generated based on a sample lesion;

obtaining a first sample image of the sample lesion corresponding to the historical treatment plan;

obtaining sample location combinations and corresponding sample segment shapes in the historical treatment plan; and obtaining the training set based on the first sample image, the sample location combinations, and the sample segment shapes of historical treatment plan.

10. The system of claim 9, wherein obtaining the training set based on the first sample image, the sample location combinations, and the sample segment shapes of the historical treatment plan includes:

obtaining processed sample location combinations that are within the location universal set, the processed sample location combinations being obtained by processing the sample location combinations based on the location universal set;

obtaining processed sample segment shapes that are within the distance universal set, the processed sample segment shapes being obtained by processing the sample segment shapes based on the distance universal set;

obtaining a sample set including the processed sample segment shapes and closed segment shapes, the closed segment shapes corresponding to the candidate location combinations excluding the processed sample location combinations; and obtaining the training set by including the first sample image, the processed sample location combinations, and the sample set of the historical treatment plan.

11. The system of claim 10, wherein the training process includes:
    initializing the preliminary model; and
    obtaining the segment shape estimation model by updating the initialized preliminary model using an iteration process including a plurality of iterations, at least one of the plurality of iterations of the iteration process including:
        obtaining one of the plurality of training sets;
        generating estimated segment shapes corresponding to the plurality of candidate location combinations by inputting the first sample image of the training set into an intermediate model, the intermediate model being the initialized preliminary model in a first iteration of the plurality of iterations of the iteration process or a previously updated model generated in a previous iteration in the iteration process;
        determining a value of a loss function based on the estimated segment shapes and the sample set in the training set;
        determining whether a termination condition is satisfied;
    in response to determining that the termination condition is not satisfied,
        generating an updated model by updating the intermediate model based on the value of the loss function; and
        initiating a next iteration; and
    designating the intermediate model in a last iteration of the plurality of iterations of the iteration process as the segment shape estimation model.

12. The system of claim 11, wherein the value of the loss function is determined based on sparsity of the sample set, the sparsity of the sample set relating to the closed segment shapes in the sample set.

13. The system of claim 11, wherein the training set includes at least one of a second sample image of normal tissue surrounding the sample lesion, a third sample image of the sample lesion, or sample radiation information of the historical treatment plan, the sample radiation information including at least one of a sample output dose, a sample dose output rate, a sample dose per pulse, or a sample dose distribution in the sample lesion.

14. The system of claim 13, wherein the sample radiation information is predicted based on the first sample image of the sample lesion, the second sample image of normal tissue surrounding the sample lesion, and the third sample image of the sample lesion.

15. The system of claim 13, wherein the at least one of the plurality of iterations of the iteration process includes:
    generating the estimated segment shapes by inputting at least one of the second sample image, the third sample image, or the sample radiation information of the training set into the intermediate model.

16. A system, comprising:
    at least one storage device including a set of instructions; and
    at least one processor configured to communicate with the at least one storage device, wherein when executing the set of instructions, the at least one processor is configured to direct the system to perform operations including:
        obtaining a preliminary model;
        obtaining a location universal set including a plurality of discrete candidate location combinations; and
        obtaining a segment shape estimation model by iteratively training a preliminary model based on the location universal set, the segment shape estimation model being configured to estimate, based on input data, a plurality of target location combinations in a target treatment plan for performing radiotherapy on a lesion using a radiation device and a plurality of target segment shapes of a collimator of the radiation device, the input data including a first target image of the lesion, each of the plurality of target segment shapes corresponding to one of the plurality of target location combinations, one of the plurality of target location combinations indicating a location of the collimator relative to the lesion.

17. The system of claim 16, wherein the plurality of target location combinations are within the plurality of discrete candidate location combinations of the location universal set.

18. The system of claim 16, wherein the training a preliminary model based on the location universal set comprises:
    determining training data, the training data including a plurality of training sets determined based on the location universal set;
    training the preliminary model based on the training data.

19. The system of claim 18, wherein one of the plurality of training sets is determined by:
    obtaining a historical treatment plan previously generated based on a sample lesion;
    obtaining a first sample image of the sample lesion corresponding to the historical treatment plan;
    obtaining sample location combinations and corresponding sample segment shapes in the historical treatment plan; and
    obtaining the training set based on the first sample image, the sample location combinations, the sample segment shapes of historical treatment plan, and the location universal set.

20. A method implemented on a machine including one or more processors and one or more storage devices, comprising:
    obtaining input data relating to a target treatment plan for performing radiotherapy on a lesion using a radiation device, the input data including a first target image of the lesion;
    obtaining a segment shape estimation model; and
    estimating, based on the segment shape estimation model and the input data, a plurality of target location combinations of the target treatment plan and a plurality of target segment shapes of a collimator of the radiation device, one of the plurality of target location combinations indicating a location of the collimator relative to the lesion, each of the plurality of target segment shapes corresponding to one of the plurality of target location combinations.

* * * * *